US008691799B2

(12) United States Patent
Sebti et al.

(10) Patent No.: US 8,691,799 B2
(45) Date of Patent: *Apr. 8, 2014

(54) MATERIALS AND METHODS FOR TREATMENT OF CANCER AND IDENTIFICATION OF ANTI-CANCER COMPOUNDS

(75) Inventors: Said M. Sebti, Tampa, FL (US); Richard Jove, Duarte, CA (US)

(73) Assignee: University of South Florida, Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/209,937

(22) Filed: Aug. 15, 2011

(65) Prior Publication Data

US 2012/0004169 A1    Jan. 5, 2012

Related U.S. Application Data

(63) Continuation of application No. 10/472,056, filed as application No. PCT/US02/11157 on Mar. 28, 2002, now Pat. No. 7,998,947.

(60) Provisional application No. 60/279,104, filed on Mar. 28, 2001.

(51) Int. Cl.
*A61K 31/56* (2006.01)
*A01N 45/00* (2006.01)

(52) U.S. Cl.
USPC .......................................... 514/177; 514/171

(58) Field of Classification Search
USPC ................................................ 514/177, 171
See application file for complete search history.

(56) References Cited

U.S. PATENT DOCUMENTS

| 4,867,978 A | 9/1989 | Gold |
| 4,921,963 A | 5/1990 | Skov et al. |
| 5,681,950 A | 10/1997 | Echeverri-Lopez et al. |
| 5,683,698 A | 11/1997 | Chavali et al. |
| 5,925,356 A | 7/1999 | Subbiah |
| 5,962,527 A | 10/1999 | Pezzuto et al. |
| 6,149,912 A | 11/2000 | Gubarev et al. |
| 6,200,780 B1 | 3/2001 | Chen et al. |
| 6,265,160 B1 | 7/2001 | Leonard |
| 6,531,645 B1 | 3/2003 | Sebti et al. |
| 6,914,158 B2 | 7/2005 | Webber et al. |
| 6,998,394 B2 | 2/2006 | Tomassini et al. |
| 7,108,870 B2 | 9/2006 | Sangwan et al. |
| 2003/0018003 A1 | 1/2003 | Sebti |
| 2004/0138189 A1 | 7/2004 | Sebti et al. |
| 2005/0049299 A1 | 3/2005 | Aggarwal |
| 2007/0123502 A1 | 5/2007 | Turkson et al. |

FOREIGN PATENT DOCUMENTS

| WO | WO 01/97828 A2 | 12/2001 |
| WO | WO 2005/082392 A1 | 9/2005 |

OTHER PUBLICATIONS

Kupchan et al. J. of Org. Chem. 1970, vol. 55, No. 9, pp. 2891-2894.*
Fernandes et al. Int. J. Cancer, 1999, vol. 83, pp. 564-570.*
Bowman, T. et al. "STATs in oncogenesis" *Oncogene*, 2000, 19:2474-2488.
Bowman, T. et al. "Signal transducers and activators of transcription: Novel targets for anticancer therapeutics" *Cancer Control*, 1999, 6(5):427-435.
Duncan, K.L. et al. "Cucurbitacin E-induced disruption of the actin and vimentin cytoskeleton in prostate carcinoma cells" *Biochem Pharmacol*, 1996, 52:1553-1560.
Duncan, M.D. and K.L. Duncan "Cucurbitacin E targets proliferating endothelia" *J. Surg. Res.*, 1997, 69:55-60.
Konoshima, T. et al. "Inhibitory effects of cucurbitane triterpenoids on Epstein-Barr Virus activation and two-stage carcinogenesis of skin tumor. II" *Biol. Pharm. Bull.*, 1995, 18(2):284-287.
Musza, L.L. et al. "Cucurbitacins, cell adhesion inhibitors from *Conobea scoparioides*" *J. Nat. Prod.*, 1994, 57:1498-1502.
Smit, H.F. et al. "Inhibition of T-lymphocyte proliferation by cucurbitacins from *Picrorhiza scrophulariaeflora*" *J. Nat. Prod.*, 2000, 63:1300-1302.
Turkson, J. and Jove, R. "STAT proteins: novel molecular argets for cancer drug discovery" *Oncogene*, 2000, 19:6613-6626.
Witkowski, A. et al. "Inhibition of the biosynthesis of deoxyribonucleic acid, ribonucleic acid and protein in HeLa S3 cells by cucurbitacins, glucocorticoid-like cytotoxic triterpenes" *Biochem Pharmacol*, 1984, 33:995-1004.
Birch at al. "A randomized study of etoposide and carboplatin with or without paclitaxel in the treatment of small cell lung cancer" *Semin. Oncol.*, 1997, S12-135-S12-137, vol. 24, No. 4 Suppl., abstract only.
Sun, J. at al. "Cucurbitacin Q: a selective STAT3 activation inhibitor with potent antitumor activity" *Oncogene*, 2008, 27:1344.
Kupchan, S. Morris et al. "Tumor Inhibitors. Active Principles of *Acnistus arborescens*. Isolation and Structural and Spectral Studies of Withaferin A and Withacnistin" *The Journal of Organic Chemistry* 1969, 34, No. 12:3858-3866.
Gura, Trisha "Systems for Identifying New Drugs are Often Faulty" *Science*, New Series, 1997, 278 (5340):1041-1042.

(Continued)

*Primary Examiner* — Samira Jean-Louis
(74) *Attorney, Agent, or Firm* — Saliwanchik, Lloyd & Eisenschenk

(57) ABSTRACT

The subject invention pertains to the treatment of tumors and cancerous tissues and the prevention of tumorigenesis and malignant transformation through the modulation of JAK/STAT3 intracellular signaling. The subject invention concerns pharmaceutical compositions containing cucurbitacin I, or a pharmaceutically acceptable salt or analog thereof. Another aspect of the invention concerns methods of inhibiting the growth of a tumor by administering a cucurbitacin I, or a pharmaceutically acceptable salt or analog thereof, to a patient, wherein the tumor is characterized by the constitutive activation of the JAK/STAT3 intracellular signaling pathway. The present invention further pertains to methods of moderating the JAK and/or STAT3 signaling pathways in vitro or in vivo using cucurbitacin I, or a pharmaceutically acceptable salt or analog thereof. Another aspect of the present invention concerns a method for screening candidate compounds for JAK and/or STAT3 inhibition and anti-tumor activity.

19 Claims, 12 Drawing Sheets

(56) References Cited

OTHER PUBLICATIONS

Golub, T.R. et al. "Molecular classification of cancer: Class discovery and class prediction by gene expression monitoring" *Science*, 1999, 286:531-537.

Sun J., et al., "CucurbitacinQ: a selective STAT3 activation inhibitor with potent antitumor activity" *Oncogene*, 2005, 24, 3236-3245.

Fuller, R.W. et al. "Cucurbitacins: Differential cytotoxicity, dereplication and first isolation from *Gonystylus keithii*" *J. Natural Products*, 1994, 57(10):1442-1445.

Ni et al. "Inhibition of constitutively activated Stat 3 signaling pathway suppresses growth of prostate cancer cells" *Cancer Res.*, 2000, 60:1225-1228.

Heim, M.H. et al. "The Jak-STAT pathway: specific signal transduction from the cell membrane to the nucleus" *Euro. J. Clin. Invest.*, 1996, 26:1-12.

Kupchan, S.M. "Tumor Inhibitors XXIII. The Cytotoxic Principles of Marah Oreganus H." *J. Med. Chem.*, 1967, 10(5):976-979.

\* cited by examiner

JSI-124
Cucurbitacin I

FIG. 5A
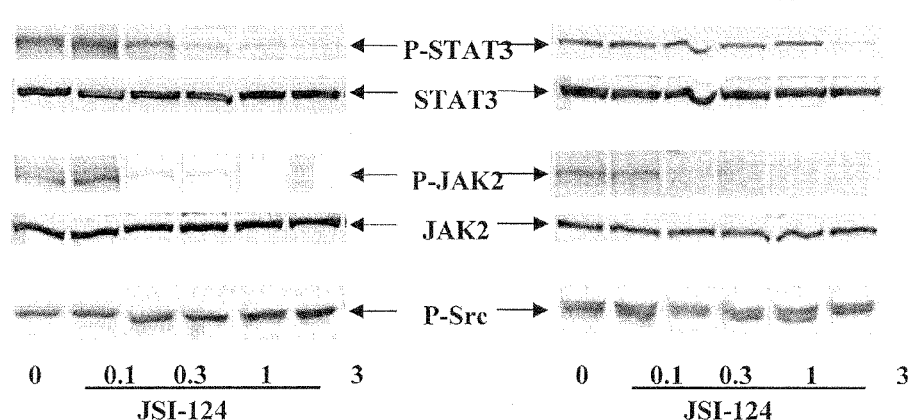
FIG. 5B
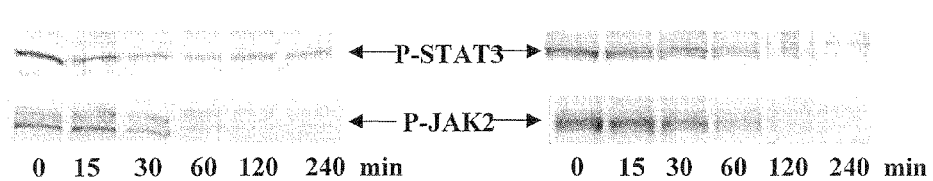
FIG. 5C

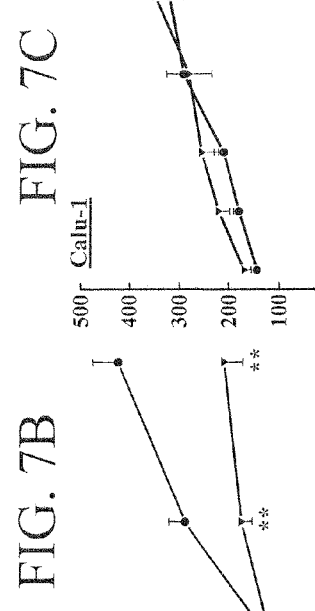
FIG. 7A
FIG. 7B
FIG. 7C
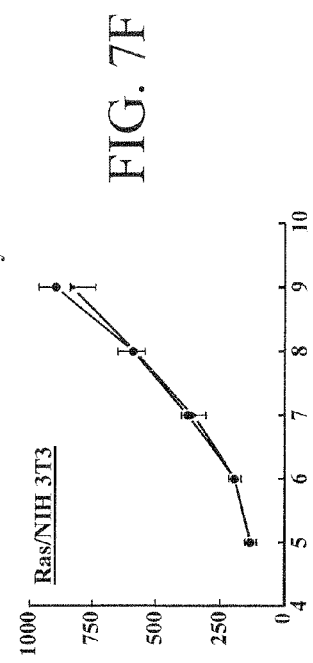
FIG. 7D
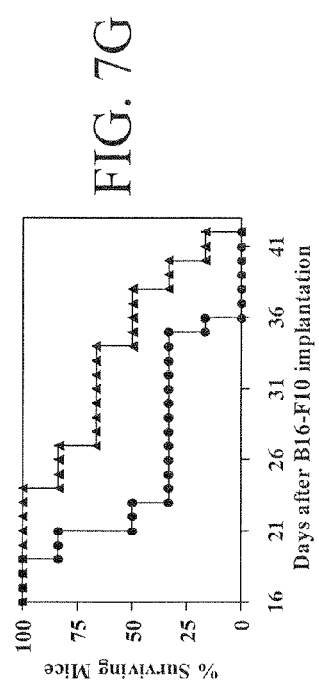
FIG. 7F
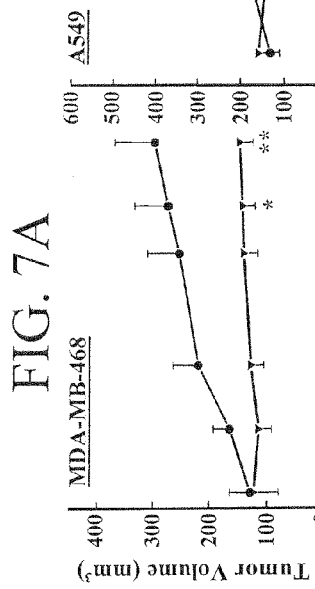
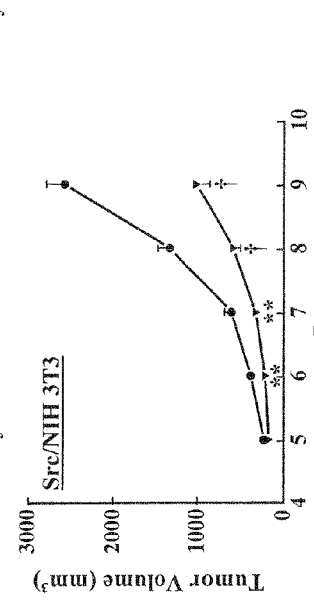
FIG. 7E
FIG. 7G

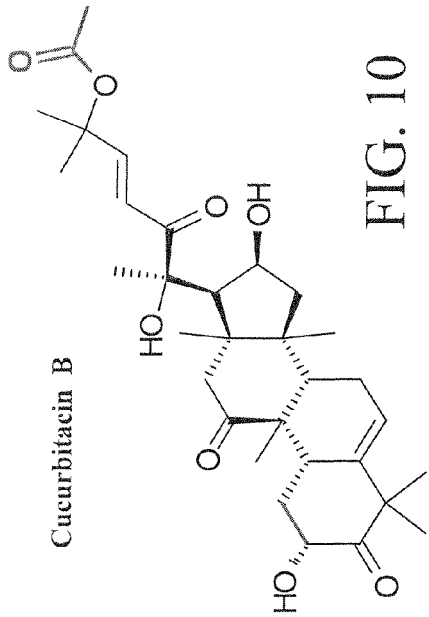
FIG. 9 Cucurbitacin A
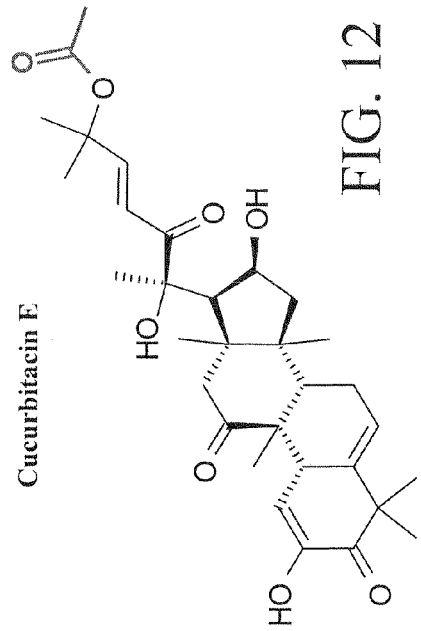
FIG. 10 Cucurbitacin B
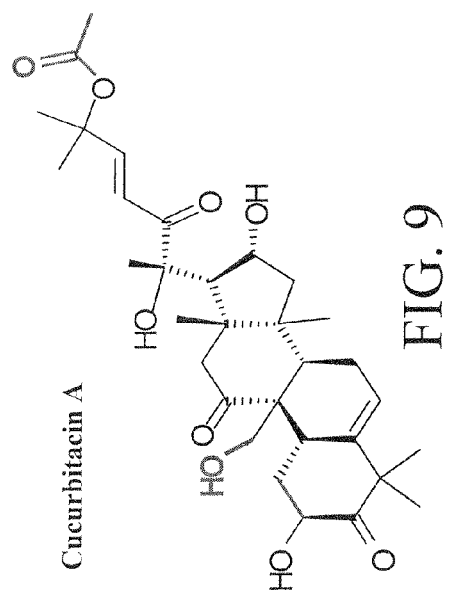
FIG. 11 Cucurbitacin D
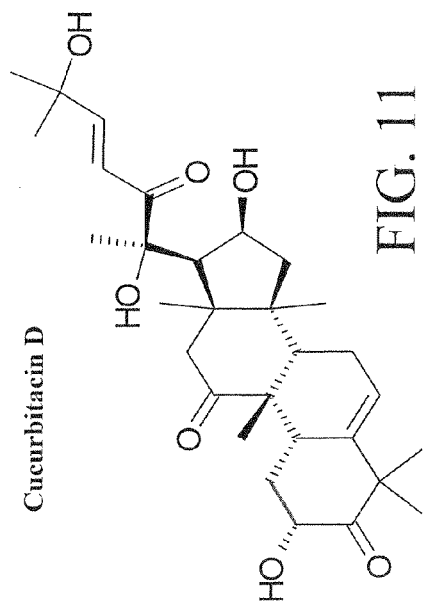
FIG. 12 Cucurbitacin E Tetrahydro-cucurbitacin I Cucurbitacin Q

| Name | P-STAT3 (IC50) | P-JAK2 (IC50) | in vivo antitumor activity % inhibition | 10μM morphology after 4hr treatment |
|---|---|---|---|---|
| Cucurbitacin A NSC # 94743 | >10 | 1.2 ± 0.6 | 16% |  |
| Cucurbitacin B NSC # 49451 | 3.9 ± 1.8 | 0.2 ± 0.09 | 40% at 0.2 mpk/dry | 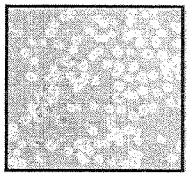 |
| Cucurbitacin D NSC # 308606 | 7.9 ± 0.8 | 0.24 ± 0.02 | ND | 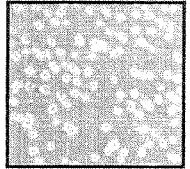 |
| Cucurbitacin E NSC # 106399 | 0.8 ± 0.3 | 0.2 ± 0.1 | 42% |  |
| Cucurbitacin I NSC # 521777 (JSI-124) | 0.2 ± 0.09 | 0.2 ± 0.06 | 45% (p < 0.05) |  |
| Tetrahydro-cucurbitacin I NSC # 112164 | 2.0 ± 0.8 | 1.3 ± 1.0 | 52% (p < 0.05) | 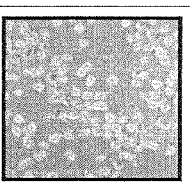 |
| Cucurbitacin Q NSC # 135075 | 2.3 ± 1.1 | >10 | 57% (p < 0.05) | 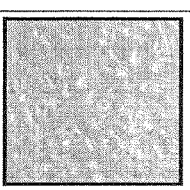 |
FIG. 17

SEQUENCE LISTING

```
<160> NUMBER OF SEQ ID NOS: 1

<210> SEQ ID NO 1
<211> LENGTH: 24
<212> TYPE: DNA
<213> ORGANISM: Artificial Sequence
<220> FEATURE:
<223> OTHER INFORMATION: Oligonucleotide probe

<400> SEQUENCE: 1
agcttcattt cccgtaaatc ccta                                           24
```

MATERIALS AND METHODS FOR TREATMENT OF CANCER AND IDENTIFICATION OF ANTI-CANCER COMPOUNDS

CROSS-REFERENCE TO RELATED APPLICATIONS

The present application is a continuation of U.S. application Ser. No. 10/472,056, filed Mar. 8, 2004, now U.S. Pat. No. 7,998,947, which is the National Stage of International Application Number PCT/US2002/011157, filed Mar. 28, 2002, which claims the benefit of U.S. Provisional Patent Application Serial No. 60/279,104, filed Mar. 28, 2001.

GOVERNMENT SUPPORT

This invention was made with government support under Grant Number P01 CA078038 awarded by the National Institutes of Health. The government has certain rights in the invention.

BACKGROUND OF INVENTION

The signal transducers and activators of transcription (STATs) are key signal transduction proteins that play a dual role of transducing biological information from cell surface receptors to the cytoplasm and translocating to the nucleus where, as transcription factors, they regulate gene expression (reviewed in Stark, G. R. et al. *Annu. Rev. Biochem.*, 1998, 67:227-264; Horvath, C. M. and J. E. Darnell *Curr. Opin. Cell. Biol.*, 1997, 9:233-239, Ihle, J. N. and I. M. Kerr *Trends Genet.*, 1995, 11:69-74; Schindler, C. and J. E. Darnell *Annu. Rev. Biochem.*, 1995, 64:621-651). Mammalian cells express seven different STATs (1, 2, 3, 4, 5a, 5b, and 6). Gene knockout and other experiments implicated STATs in many important physiological functions such as immune modulation, inflammation, proliferation, differentiation, development, cell survival and apoptosis (Stark, G. R. et al. *Annu. Rev. Biochem.*, 1998, 67:227-264; Horvath, C. M. and J. E. Darnell *Curr. Opin. Cell. Biol.*, 1997, 9:233-239, Ihle, J. N. and I. M. Kerr *Trends Genet.*, 1995, 11:69-74; Schindler, C. and J. E. Darnell *Annu. Rev. Biochem.*, 1995, 64:621-651).

STAT tyrosine phosphorylation is required for their biological function. This occurs when cytokines such as interleukin-6 and interferon or growth factors such as PDGF and EGF bind their respective receptors which results in STAT protein recruitment to the inner surface of the plasma membrane in the vicinity of the cytoplasmic portion of the receptors (Ihle, J. N. et al. *Annu. Rev. Immunol.*, 1995, 13:369-398; Leaman, D. W. et al. *Faseb J.*, 1996, 10:1578-1588). Tyrosine kinases that are known to phosphorylate STATs are non-receptor tyrosine kinases such as Src and the Janus kinases, JAK1 and JAK2. Other possible tyrosine kinases that can phosphorylate STATs are peptide growth factor receptors such as PDGFR and EGFR. The cellular levels of STATs that are tyrosine phosphorylated could also be regulated by phosphotyrosine STAT phosphatases such as SHP-1 and SHP-2 (Schaper, F. et al. *Biochem J.*, 1998, 335:557-565; Stofega, M. R. et al. *J. Biol. Chem.*, 1998, 273:7112-7117; Yu, C. L. et al. *J. Biol. Chem.*, 2000, 275:599-604). Once tyrosine phosphorylated, STAT monomers dimerize via reciprocal phosphotyrosine-SH2 interactions and translocate to the nucleus where they bind DNA and regulate gene transcription (Ihie, J. N. and I. M. Kerr *Trends Genet.*, 1995, 11:69-74; Seidel, H. M. et al. *Proc. Natl. Acad. USA*, 1995, 92:3041-3045). Whereas tyrosine phosphorylation of STATs regulates dimerization, nuclear translocation and DNA-binding, serine/threonine phosphorylation is believed to regulate the transcriptional activity of STATs (Turkson, J. et al. *Mol. Cell Biol.*, 1999, 19:7519-7528).

Several lines of evidence have implicated some STAT family members in malignant transformation and tumor cell survival (Bowman, T. et al. *Cancer Control*, 1999, 6:427-435; Turkson, J and R. Jove *Oncogene*, 2000, 19:6613-6626). STAT3 involvement in oncogenesis is the most thoroughly characterized. First, STAT3 is found constitutively tyrosine phosphorylated and activated in many human cancers (Bowman, I. et al. *Cancer Control*, 1999, 6:427-435; Turkson, J and R. Jove *Oncogene*, 2000, 19:6613-6626; Bowman, T. et al. *Oncogene*, 2000, 1 9:2474-2488). This abnormal activation of STAT3 is prevalent in breast, pancreas, ovarian, head and neck, brain, and prostate carcinomas as well as melanomas, leukemias and lymphomas. In those tumors investigated, aberrant STAT3 activation is required for growth and survival (Bowman, T. et al. *Cancer Control*, 1999, 6:427-435; Turkson, J and R. Jove *Oncogene*, 2000, 19:6613-6626; Bowman, T. et al. *Oncogene*, 2000, 19:2474-2488). Second, many known oncogenes, especially those belonging to the non-receptor tyrosine kinase family such as src, induce constitutive activation of STAT3 (Yu, C. L. et al. *Science*, 1995, 269:81-83). Third, expression of a constitutively-activated mutant of STAT3, where stable dimerization was forced through disulfide covalent linkage, was shown to be sufficient to induce cell transformation and tumor growth in nude mice (Bromberg, J. F. et al. *Cell*, 1999, 98:295-303). Finally, perhaps the most compelling evidence for the requirement of STAT3 for oncogenesis and its validation as an anticancer drug target comes from experiments where a dominant negative form of STAT3 was used in cultured cells as well as in gene therapy animal experiments to show that blocking aberrant activation of STAT3 results in inhibition of tumor growth and survival and induction of apoptosis with little side effects to normal cells (Niu, G. et al. *Cancer Res.*, 1999, 59:5059-5063; Catlett-Falcone, R. et al. *Immunity*, 1999, 10:105-115).

Much of modern anticancer drug discovery approaches have focused on targeting signal transduction pathways involving receptor tyrosine kinases (e.g., ErbB2, EGFR), farnesylated proteins (e.g., Ras), and non-receptor cytosolic kinases (e.g., Raf, Mek, P13K, and Akt) (Sebti, S. *New Drug Targets and Therapies for Cancer*, 2000, 6549-6692). These important efforts resulted in several novel agents such as RTK monoclonal antibodies and RTK, farnesyltransferase, Raf, and Mek inhibitors that are presently in clinical trials, such as the Bcr-Ahl tyrosine kinase inhibitor STI-571 (GLEEVEC), which has recently been approved by the FDA for chronic myelogenous leukemia.

In contrast to the heavily exploited area described above, little has been done to target the STAT3 signaling pathway. Yet, experiments in animal models using gene therapy with a dominant negative form of STAT3 and a constitutively-active mutant o STAT3, as well as the prevalence of constitutively-activated STAT3 in many human cancers, strongly suggest that STAT3 has a causal role in oncogenesis (Bowman, T. et al. *Cancer Control*, 1999, 6:427-435; Turkson, J and. R. Jove *Oncogene*, 2000, 19:6613-6626; Bowman, T. et al. *Oncogene*, 2000, 19:2474-2488). Furthermore, the fact that constitutive activation of STAT3 induces genes such as cyclin D1, c-myc, and bcl-xl that are intimately involved in oncogenesis and tumor survival, coupled with the fact that constitutively-activated STAT3 is required for survival of some human cancer cells, further validates the STAT3 signaling pathway as a selective cancer drug discovery target (Bowman, T. et al.

Cancer Control, 1999, 6:427-435; Turkson, J and R. Jove Oncogene, 2000, 19:6613-6626; Bowman, T. et al. Oncogene, 2000, 19:2474-2488.

Based on the observations described above, some researchers have undertaken to target STAT3 for the development of novel anti-cancer drugs (reviewed in Bowman, T. et al. Cancer Control, 1999, 6:427-435; Turkson, J and R. Jove Oncogene, 2000, 19:6613-6626; and Bowman, T. et al. Oncogene, 2000, 19:2474-2488). Depending on the aberrant genetic alterations that result in constitutively tyrosine-phosphorylated, activated STAT3, several approaches can be undertaken including blocking ligand/receptor interactions, inhibiting receptor and non-receptor tyrosine kinases, activating phosphotyrosine STAT3 phosphatases, and blocking STAT3 dimerization, nuclear translocation, DNA-binding, and gene transcription. In addition, gene therapy, anti-sense, or RNAi approaches can also be attempted.

JSI-124 is a plant natural product previously identified as cucurbitacin I, a member of the cucurbitacin family of compounds that are isolated from various plant families, such as the Cucurbitaceae and Cruciferae, and that have been used as folk medicines for centuries in countries such as China and India. However, little was known about the biological activities of the various cucurbitacins until recently. Some cucurbitacins have been shown to have anti-inflammatory and analgesic as well as cytotoxic effects. Furthermore, cucurbitacins were also found to inhibit DNA, RNA and protein synthesis in HeLa cells (Witkowski, A. et al. Biochem Pharmacol, 1984, 33:995-1004) and inhibit proliferation of HeLa cells (Witkowski, A. et al. Biochem Pharmacol, 1984, 33:995-1004), endothelial cells (Duncan, M. D. and K. L. Duncan J. Surg. Res., 1997, 69:55-60) and T-lymphocytes (Smit, H. F. et al. J. Nat. Prod., 2000, 63:1300-1302). Finally, some cucurbitacins were shown to suppress skin carcinogenesis (Konoshima, T. et al. Biol. Pharm. Bull., 1995, 18:284-287), inhibit cell adhesion (Musza, L. L. et al. J. Nat. Prod., 1994, 57:1498-1502) and disrupt the actin and vimentin cytoskeleton in prostate carcinoma cells (Duncan, K. L. et al. Biochem Pharmacol, 1996, 52:1553-1560; Duncan, M. D. and K. L. Duncan J. Surg. Res., 1997, 69:55-60).

BRIEF SUMMARY OF THE INVENTION

The subject invention relates to the identification of substances capable of interfering with the signaling events leading to the abnormally elevated levels of tyrosine phosphorylated STAT3 in many human cancer cells. More specifically, the subject invention concerns the identification of substances that act as inhibitors of STAT3 activation pathways. The subject invention further concerns the treatment of tumors and cancerous tissues and the prevention of tumorigenesis and malignant transformation through the disruption of STAT3 intracellular signaling.

In one aspect, the subject invention concerns a pharmaceutical composition comprising a compound having the structure shown in FIG. 1 (also referred to herein as JSI-124 or cucurbitacin I), which is a potent suppressor of the JAK/STAT3 tumor survival pathway, and which exhibits potent antitumor activity. In another aspect, the subject invention concerns a pharmaceutical composition comprising an analog of cucurbitacin I, such as cucurbitacin A, cucurbitacin B, cucurbitacin D, cucurbitacin E, cucurbitacin Q, or tetrahydrocucurbitacin I. The pharmaceutical compositions of the subject invention are useful for treating cancer and inhibiting tumor growth, wherein the cancer or tumor is characterized by constitutive activation of the JAK2 and/or STAT3 signaling pathways.

The subject invention also concerns articles of manufacture useful in treating cancer and inhibiting tumor growth, wherein the cancer or tumor is characterized by constitutive activation of the JAK2 and/or STAT3 signaling pathways.

In another aspect, the subject invention concerns a method of inhibiting the growth of cancer cells in a patient by the administration of cucurbitacin I (JSI-124), or analogs thereof. In a further aspect, the present invention concerns methods for modulating STAT3 activity in vitro or in vivo by administering cucurbitacin I, or analogs thereof.

In a further aspect, the subject invention concerns a method of screening substances for antitumor activity using a phosphotyrosine STAT3-specific cytoblot. Using the screening method of the subject invention, modulation of STAT3 can be utilized to evaluate the antitumor efficacy of a candidate substance on a broad spectrum of cancer cell lines.

In another aspect, the subject invention concerns a kit for screening substances for antitumor activity comprising cells and a ligand specific for phosphotyrosine-STAT3 protein, wherein the ligand is directly or indirectly associated with a detectable label. Optionally, the kit can further comprise a substrate for carrying out the assay.

BRIEF DESCRIPTION OF THE DRAWINGS

FIG. 3A shows phosphotyrosine STAT3 levels in various human cell lines. Lysates from a variety of human cancer cell lines were processed for Western blotting using anti-phosphotyrosine STAT3 antibody as described in Materials and Methods. FIG. 3B shows suppression of phosphotyrosine STAT3 levels by JSI-124. v-Src-transformed NIH 3T3 cells, A549 (a lung adenocarcinoma), MDA-MB-231 (a breast carcinoma), MDA-MB-468 (a breast carcinoma) and Panc-1 (a pancreatic carcinoma) cells were treated for 4 hours with either vehicle or JSI-124 (10 μM), harvested and processed for anti-phosphotyrosine STAT3 Western blotting as described for 2a. FIG. 3C shows suppression of phosphotyrosine STAT3 levels by JSI-124 without affecting STAT3 protein levels. A549 and MDA-MB-468 cells were treated as in FIG. 3B except that the lysates were first immunoprecipitated with anti-STAT3 antibody and immunoblotted either with anti-phosphotyrosine STAT3 antibody or anti-STAT3 antibody. Data are representative of three independent experiments for FIGS. 3A, 3B, and 3C.

In FIG. 4A, v-Src-transformed NIH 3T3 cells and A549 cells were treated with vehicle or JSI-124, harvested and processed for EMSA as described under Materials and Methods. Samples in lanes 1 through 4 and 6 through 9 are from cells that were treated with vehicle control, whereas samples from lanes 5 and 10 are from cells treated with JSI-124. Lanes 2 and 3 as well as 7 and 8 are from samples supershifted with anti-STAT1 or anti-STAT3 antibodies, respectively. In FIG. 4B, v-Src-transformed NIH 3T3 cells transfected either with STAT3 (pLucTKS3)- or SRE (pRLSRE)-dependent luciferase reporters were either treated with vehicle or JSI-124 and processed for luciferase assays as described under Materials and Methods. Data are representative of two independent experiments.

FIGS. 5A-5C show the effects of JSI-124 on phosphotyrosine levels and kinase activities of JAK and Src kinases. FIG. 5A shows suppression of phosphotyrosine levels of STAT3 and JAK2 but not Src, by JSI-124. A549 and MDA-MB-468 cells were treated with various concentrations of JSI-124 and processed for immunoblotting with antibodies specific for either phosphotyrosine STAT3, phosphotyrosine JAK2 or phosphotyrosine Src as described under Methods. The membranes were also reblotted with antibodies to STAT3 and JAK2. FIG. 5B shows rapid suppression by JSI-124 of phosphotyrosine STAT3 and JAK2. A549 and MDA-MB-468 cells were treated with JSI-124 (10 µM) for various lengths of time (0-240 min) and processed as described above. FIG. 5C shows that JSI-124 does not inhibit JAK1, JAK2 and Src kinase activities. Lysates from v-Src transformed cells, A549 cells and MDA-MB-468 cells were immunoprecipitated with antibodies against JAK1, JAK2 and Src. Autophosphorylation kinase assays were then performed as described under Materials and Methods. Immunoprecipitates were incubated either with vehicle control (C), JSI-124 (J), the JAK kinase inhibitor AG490 (A) or the Ste kinase inhibitor PD 180970 (P). Data are representative of three independent experiments.

FIGS. 7A-7G show that JSI-124 increases mouse survival and inhibits tumor growth in mice of MDA-MB-468 (FIG. 7A), A-549 (FIG. 7B), B16-F10 (FIG. 7E) and v-Src/NIH 3T3 (FIG. 7D), but not Calu-1 (FIG. 7C) and Ras/NIH 3T3 cells (FIG. 7F). MDA-MB-468, A549, Calu-1, v-Src/NIH 3T3, and Ras/NIH 3T3, cells were implanted s.c. in nude mice, whereas B16-F10 cells were implanted s.c. in C57 black mice. When the tumors reached an average size of about 100 $mm^3$-150 $mm^3$, animals were randomized (five animals per group; two tumors per animal) and treated with either vehicle (circle) or 1 mg/kg/day JSI-124 (triangle) as described under Materials and Methods. Each measurement represents an average of ten tumors. Data are representative of four (B16-F10), three (A549, v-Src/NIH 3T3, and Ras/NIH 3T3) and two (MDA-MB-468 and Calu-1) independent experiments († designate P<0.01; **, P<0.05; *, P=0.08). For the mouse survival studies, C57 black mice were implanted s.c. with B16-F10 cells and on day 5 after implantation, the mice were randomized (6 animals per group) and treated with either vehicle (circles) or JSI-124 (triangles) (1 mg/Kg/day) for 25 days. Percent surviving mice was determined by monitoring the death of mice over a period of 42 days until all mice died. Data are representative of two independent experiments carried out with 12 mice each (6; vehicle control-treated and 6; JSI-124-treated). For statistical analysis: for each of the 2 experiments, control animals were compared to JSI-124 animals with respect to survival using the permutation log rank test as implemented in the statistical software package, Proc-StatXact. The results of both experiments were pooled in a stratified analysis and gave a p-value of 0.01.

FIG. 9 shows the chemical structure of cucurbitacin A, a cucurbitacin analog of the subject invention.

FIG. 10 shows the chemical structure of cucurbitacin B, a cucurbitacin analog of the subject invention.

FIG. 11 shows the chemical structure of cucurbitacin D, a cucurbitacin analog of the subject invention.

FIG. 12 shows the chemical structure of cucurbitacin E, a cucurbitacin analog of the subject invention.

FIG. 16 shows that cucurbitacin I, which inhibits both phospho STAT3 and phospho JAK2 levels, inhibits tumor growth. In contrast, cucurbitacin A, which inhibits only phospho JAK2, but no phospho STAT3 levels, did not significantly inhibit tumor growth. Cucurbitacin Q which inhibits phospho STAT3 but not phospho JAK2 levels was as potent as cucurbatacin I at inhibiting tumor growth.

FIG. 17 is a table showing that cucurbitacin Q, tetrahydro cucurbitacin cucurbitacin I, and cucurbitacin E inhibit tumor growth, whereas curbitacin A did not and cucurbitacin B was toxic at 1 mg/kg/day. At 200 µg/kg/day, cucurbitacin B was not toxic.

BRIEF DESCRIPTION OF THE SEQUENCES

SEQ ID NO. 1 is a $^{32}P$-radiolabeled oligonucleotide probe that binds STAT1 and STAT3.

DETAILED DISCLOSURE OF THE INVENTION

The subject invention pertains to compounds capable of interfering with the signaling events leading to the abnormally elevated levels of tyrosine phosphorylated STAT3 in many human cancers.

Figure 1:
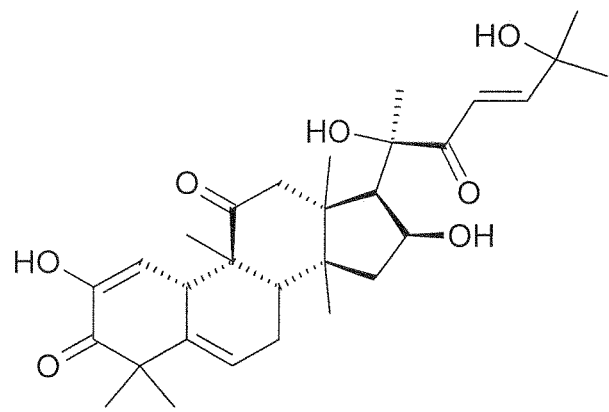
FIG. 1 shows the chemical structure of JSI-124 (cucurbitacin I), which was identified from the NCI diversity set using a phosphotyrosine STAT3 high throughput cytoblot assay.

In one aspect, the subject invention concerns a pharmaceutical composition comprising a compound having the structure shown in FIG. 1 (also referred to herein as JSI-124 or cucurbitacin I), which is a potent suppressor of the JAK/STAT3 tumor survival pathway, and which exhibits potent antitumor activity. In another aspect, the present invention concerns a pharmaceutical composition comprising an analog of cucurbitacin I. In a further aspect, the present invention concerns a pharmaceutical composition comprising an analog of curbitacin I selected from the group consisting of cucurbitacin A, cucurbitacin B, cucurbitacin D, cucurbitacin E, cucurbitacin Q, and tetrahydro-cucurbitacin I. The chemical structures of the cucurbitacin analogs are shown in FIGS. 9-14, respectively.

In another aspect, the subject invention concerns a method of inhibiting the growth of cancer cells in a patient by the administration of cucurbitacin I (JSI-124), or analogs thereof. The method of the subject invention is useful in treating cancer and inhibiting tumor growth, wherein the cancer or tumor is characterized by constitutive activation of the JAK2 and/or STAT3 signaling pathways. Treatment of cancer involves a decrease of one or more symptoms associated with the particular cancer. Preferably, the treatment involves a decrease in tumor growth rate, particularly where the tumor is characterized by constitutive activation of the JAK2 and/or STAT3 signaling pathways.

The present inventors have demonstrated that JSI-124 and analogs of JSI-124 reduce the levels of phosphotyrosine constitutively-activated STAT3 in many human cancer cell lines including pancreatic, lung and breast carcinomas. Without being bound by theory, this suppression in the levels of constitutively-activated STAT3 results in blockade of STAT3 DNA-binding activity and STAT3-mediated gene transcription. JSI-124 was highly selective for disrupting STAT3 signaling over other pivotal oncogenic and tumor survival pathways. For example, in two cell lines, the human lung adenocarcinoma A549 and the human breast carcinoma MDA-MB-468, JSI-124 did not inhibit the constitutive activation of the Ser/Thr protein kinase B, PKB/Akt, indicating that the phosphoinositide-3-kinase (PI3K)/Akt survival pathway is not a target for JSI-124. Similarly, the Ras/Raf/Mek/Erk oncogenic signaling pathway was not inhibited by JSI-124 in these two cell lines. Finally, the constitutive activation of Jun kinase in A549 and MDA-MB-468 was not affected by JSI-124, indicating that the stress activated protein kinase signaling pathway is not targeted by JSI-124.

A large number of human cancers rely on the PI3K/Akt and the Ras/Raf/Mek/Erk pathways to induce malignant transformation and tumor survival. For example, the great majority of tumors overexpress the ErbB family of receptors such as EGFR and ErbB2 and contain mutant forms of Ras. These RTK and Ras genetic alterations result in constitutive activation of the PI3K/Akt and Ras/Raf/Mek/Erk pathways. The fact that JSI-124 inhibits tumor growth and blocks STAT3 signaling without inhibiting the constitutive activation of Akt and Erk1/Erk2 suggests that its ability to inhibit the growth of A549 and MDA-MB-468 in nude mice does not depend on blocking Akt and Erk activation. This also suggests that JSI-124 may be more selective towards inhibiting the growth of tumors with constitutively-activated STAT3. Consistent with this, it was found that v-Src-transformed NIH 3T3 tumors which depend on constitutively-activated STAT3 for malignant transformation are sensitive to JSI-124 antitumor activity in nude mice. In contrast, oncogenic Ras-transformed NIH 3T3 tumors, where STAT3 is not constitutively-activated, were resistant to JSI-124. Furthermore, the fact that JSI-124 inhibited the growth in mice of the human lung adenocarcinoma (A-549), the human breast carcinoma (MDA-MB-468) and the murine melanoma (B16-F10) all of which express constitutively activated STAT3 but not the human lung adenocarcinoma (Calu-1) that has very low levels of tyrosine phosphorylated STAT3 gives further support to the notion that the ability of JSI-124 to inhibit tumor growth depends on an aberrantly activated STAT3 signaling pathway. Importantly, JSI-124 also significantly increased the survival of immunologically-competent mice implanted with B16-F10 murine melanoma.

The ability of JSI-124 to suppress the cellular levels of phosphotyrosine-STAT3 but not phospho-Erk1/2, phospho-JNK, and phospho-Akt suggested that a STAT3 tyrosine kinase is a possible molecular target for JSI-124. Consistent with a direct inhibition of the enzymatic activity of a tyrosine kinase is the fact that suppression of the STAT3 phosphotyrosine levels was rapid (observed as early as 30 min and complete after only 2 hr of treatment). There are two well-characterized STAT3 tyrosine kinases: JAK and Src kinase. Because phosphotyrosine JAK2 levels were also reduced by JSI-124 this suggested that JAK2 is likely not the target. This was confirmed by in vitro kinase assays where JAK2 and JAK1 enzymatic activities were inhibited by AG490, a known JAK inhibitor, but not JSI-124. Similarly, Src kinase activity was inhibited in vitro by the known Src kinase inhibitor PD180970 but not JSI-124, indicating that Src kinase is not a target. The receptor tyrosine kinase EGFR that is believed also to phosphorylate STAT3 is most likely not a target either since EGF-stimulation of EGFR tyrosine phosphorylation in the breast cell line MCF-10A and EGFR-overexpressing NIH 3T3 cells was inhibited only minimally by JSI-124 (data not shown).

Without being bound by theory, reduction in phosphotyrosine levels could be due either to inhibition of protein tyrosine kinases or activation of protein phosphotyrosine phosphatases (PTPs). STAT3 is known to be phosphotyrosine dephosphorylated by two PTPs, SHP-1 and SHP-2 (Schaper, F. et al. *Biochem. J.*, 1998, 335:557-565; Yu, C. L. et al. *J. Biol. Chem.*, 2000, 275:599-604), and JSI-124 could downregulate phosphotyrosine-STAT3 levels by promoting the protein phosphatase activities of SHP-1 and SHP-2. Alternatively, JSI-124 could also activate physiological inhibitors that are known to directly or indirectly downregulate STAT3 activation. These include suppressors of cytokine signaling (SOCS), STAT-induced STAT inhibitor (SSI), JAK binding protein (JAB), and STAT3 interacting protein (StP1) (Turkson, J. and R. Jove *Oncogene*, 2000, 19:6613-6626).

According to the method of the subject invention, cucurbitacin I, or a pharmaceutically acceptable salt or analog thereof, is administered to a patient in an effective amount to decrease the constitutive levels of JAK2 activity, constitutive levels of STAT3 activity, or constitutive levels of both JAK2 and STAT3 activity. The cucurbitacin I, or a pharmaceutically acceptable salt or analog thereof, can be administered prophylactically before tumor onset, or as treatment for existing tumors.

In one embodiment of the method of the present invention, cucurbitacin I, or a pharmaceutically acceptable salt or analog thereof, is administered to a patient, wherein the cucurbitacin analog administered exhibits inhibition toward both JAK2 and STAT3 constitutive activity. In another embodiment of the method of the subject invention, a cucurbitacin analog is administered to a patient, wherein the cucurbitacin analog administered exhibits inhibition toward constitutive STAT3 activity, but not constitutive JAK2 activity. Preferably, the patient is suffering from a form of cancer that is characterized by constitutive activation of only the JAK2 signaling pathway, by constitutive action of only the STAT3 signaling pathway, or by constitutive action of both the JAK2 and STAT3 signaling pathway.

Cucurbitacin analogs can be used according to the methods of the subject invention so long as the analogs exhibit the desired biological activity. Biological activity characteristics can be evaluated using a high-throughput system, such as the method of the subject invention (the cytoblot assay), described in detail below, or other methods disclosed herein and/or known to those of ordinary skill in the art.

A cucurbitacin analog having the capability to modulate the JAK and/or STAT3 signaling pathway would be considered to have the desired biological activity in accordance with the subject invention. For therapeutic applications, an analog of the subject invention preferably has the capability to inhibit activation of the JAK and/or STAT3 signaling pathway. Inhibition of STAT3 signaling by cucurbitacin I, and analogs thereof, selectively promotes apoptosis in tumor cells that harbor constitutively activated STAT3. Therefore, the desirable goals of promoting apoptosis ("programmed cell death")

of selective cancerous cells and suppression of malignant transformation of normal cells within a patient are likewise accomplished through administration of antagonists or inhibitors of STAT 3 signaling of the present invention, which can be administered as simple compounds or in a pharmaceutical formulation.

Figure 8:
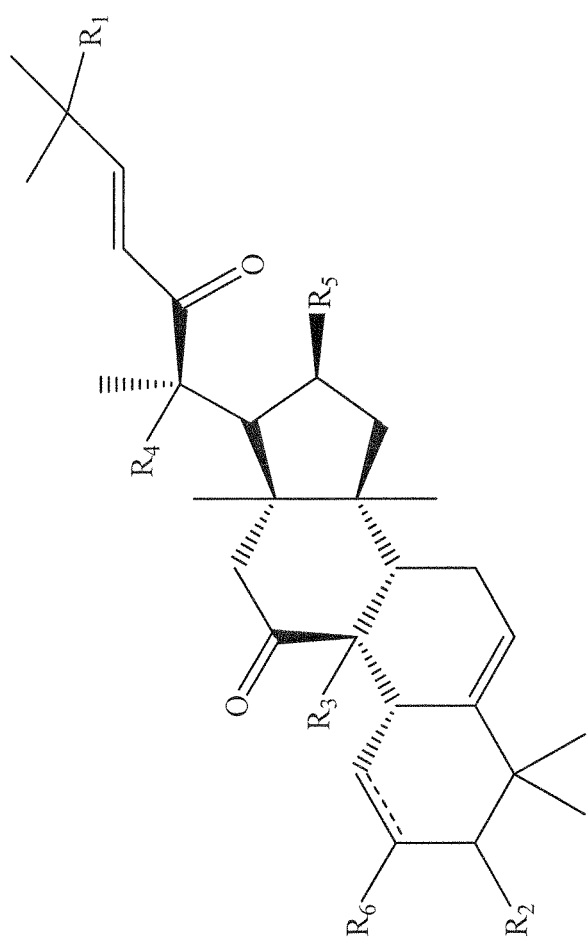
FIG. 8 shows chemical structure 1, representing cucurbitacin analogs of the subject invention.
Figure 14:
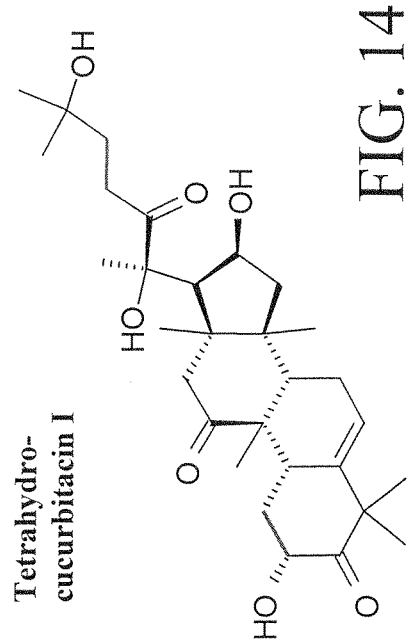
FIG. 14 shows the chemical structure of tetrahydro-cucurbitacin I, a cucurbitacin analog of the subject invention.
Figure 13:
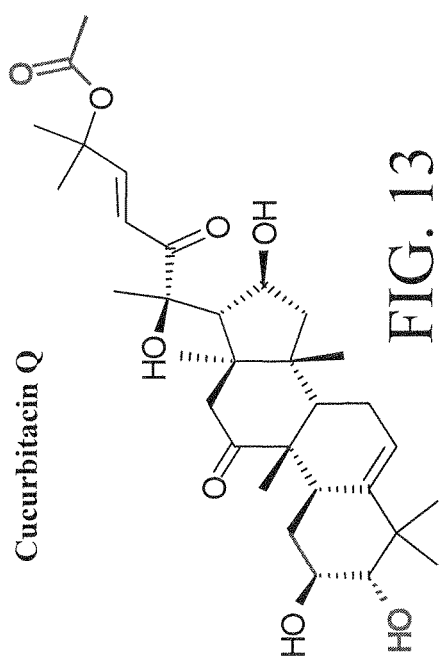
FIG. 13 shows the chemical structure of cucurbitacin Q, a cucurbitacin analog of the subject invention.

The cucurbitacin analogs of the subject invention include naturally occurring analogs of cucurbitacin I and synthetic analogs of cucurbitacin I. Cucurbitacin analogs of the subject invention can be substituted at various positions. FIG. 8 shows a chemical structure (structure I) representing cucurbitacin analogs of the subject invention.

Referring to each of the chemical structures shown in FIG. 8 (structure I). $R_1$ $R_2$, $R_3$, $R_4$, $R_5$, and $R_6$ can each be the same or different. $R_1$, $R_2$, $R_3$, $R_4$, $R_5$, and $R_6$ can each be H, O, hydroxyl, alkyl, alkenyl, alkynyl, halogen, alkoxy, aryl, or heteroaryl.

As used in the specification, the term "alkyl" refers to a straight or branched chain alkyl moiety. In one embodiment, the alkyl moiety is $C_{1-8}$ alkyl, which refers to an alkyl moiety having from one to eight carbon atoms, including for example, methyl, ethyl, propyl, isopropyl, butyl, tent-butyl, pentyl, hexyl, octyl, and the like. In another embodiment, the alkyl moiety is $C_{1-3}$ alkyl.

The term "alkenyl" refers to a straight or branched chain alkyl moiety having in addition one or more carbon-carbon double bonds, of either E or Z stereochemistry where applicable. In one embodiment, the alkenyl moiety is $C_{2-6}$ alkenyl, which refers to an alkenyl moiety having two to six carbon atoms. This term would include, for example, vinyl, 1-propenyl, 1- and 2- butenyl, 2- methyl-2-propenyl, and the like.

The term "alkynyl" refers to a straight or branched chain alkyl moiety having in addition one or more carbon-carbon triple bonds. In one embodiment, the alkynyl moiety is $C_{2-6}$ alkynyl, which refers to an alkynyl moiety having two to six carbon atoms. This term would include, for example, ethynyl, 1-propynyl, 1- and 2- butynyl, 1- methyl-2-butynyl, and the like.

The term "alkoxy" refers to an alkyl-O- group, in which the alkyl group is as previously described.

The term "halogen" refers to fluorine, chlorine, bromine, or iodine.

The term "aryl" refers to an aromatic carbocyclic ring, optionally substituted with, or fused with, an aryl group. This term includes, for example, phenyl or napthyl.

The term "heteroaryl" refers to aromatic ring systems of five to ten atoms of which at least one atom is selected from O, N, and S, and optionally substituted with an aryl group substituent. This term includes for example furanyl, thiophenyl, pyridyl, indolyl, quinolyl, and the like.

The term "aryl group substituent" refers to a substituent chosen from halogen, CN, $CF_3$, $CH_2F$, and $NO_2$.

The term "optionally substituted" means optionally substituted with one or more of the groups specified, at any available position or positions.

It will be appreciated that the cucurbitacin analogs of the subject can contain one or more asymmetrically substituted carbon atoms (chiral centers). The presence of one or more of these asymmetric centers in an analog of the chemical structure shown in FIG. 8 can give rise to stereoisomers, and in each case the invention is to be understood to extend to all such stereoisomers, including enantiomers and diastereomers, and mixtures including racemic mixtures thereof, having JAK and/or STAT3 pathway inhibitory activity.

The precise dosage will depend on a number of clinical factors, for example, the type of patient (such as human, non-human mammal, or other animal), age of the patient, and the particular cancer under treatment and its aggressiveness. A person having ordinary skill in the art would readily be able to determine, without undue experimentation, the appropriate dosages required to achieve the appropriate clinical effect.

A "patient" refers to a human, non-human mammal, or other animal in which inhibition of the JAK/STAT signaling pathway would have a beneficial effect. Patients in need of treatment involving inhibition of the JAK/STAT signaling pathway can be identified using standard techniques known to those in the medical profession.

The compounds of the subject invention, including cucurbitacin I, and analogs thereof, can be obtained through a variety of methods known in the art. For example, cucurbitacin I can be isolated and purified from various plant families, such as the Cucurbitaceae and Cruciferae. Cucurbitacin analogs of the subject invention can be synthesized using methods of organic synthesis known to those of ordinary skill in the art.

A further aspect of the present invention provides a method of modulating the activity of the JAK/STAT signaling pathway and includes the step of contacting cells or tissue with cucurbitacin I, or analogs thereof, inhibiting activity of the JAK/STAT signaling pathway. The method can be carried out in vivo or in vitro.

While cucurbitacin I and cucurbitacin analogs can be administered as an isolated compound, it is preferred to administer these compounds as a pharmaceutical composition. The subject invention thus further provides pharmaceutical compositions comprising cucurbitacin I, or an analog thereof, as an active agent, or physiologically acceptable salt(s) thereof, in association with at least one pharmaceutically acceptable carrier or diluent. The pharmaceutical composition can be adapted for various routes of administration, such as enteral, parenteral, intravenous, intramuscular, topical, subcutaneous, and so forth. Administration can be continuous or at distinct intervals, as can be determined by a person of ordinary skill in the art.

The compounds of the subject invention can be formulated according to known methods for preparing pharmaceutically useful compositions. Formulations are described in a number of sources which are well known and readily available to those skilled in the art. For example, *Remington's Pharmaceutical Sciences*(Martin E W [1995] Easton Pa., Mack Publishing Company, 19$^{th}$ ed.) describes formulations which can be used in connection with the subject invention. Formulations suitable for administration include, for example, aqueous sterile injection solutions, which may contain antioxidants, buffers, bacteriostats, and solutes which render the formulation isotonic with the blood of the intended recipient; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the formulations of the subject invention can include other agents conventional in the art having regard to the type of formulation in question.

The cucurbitacin compound of the present invention include all hydrates and salts that can be prepared by those of skill in the art. Under conditions where the compounds of the present invention are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, alpha-ketoglutarate, and alpha-glycerophosphate. Suitable inorganic salts may also be formed, including hydrochloride, sulfate, nitrate, bicarbonate, and carbonate salts.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, or sugar and the like. A syrup or elixir may contain the active compound, sucrose or fructose as a sweeting agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may incorporated into sustained-release preparations and devices.

According to the method of the subject invention, cucurbitacin I, or a pharmaceutically acceptable salt or analog thereof can be administered to a patient by itself, or co-administered with another compound, including cucurbitacin I, or a pharmaceutically acceptable salt or analog thereof. Co-administration can be carried out simultaneously (in the same or separate formulations) or consecutively. Furthermore, according to the method of the subject invention, cucurbitacin I, or a pharmaceutically acceptable salt or analog thereof, can be administered to a patient as adjunctive therapy. For example, cucurbitacin I, or a pharmaceutically acceptable salt or analog thereof, can be administered to a patient in conjunction with chemotherapy.

Thus, the cucurbitacin compounds of the subject invention (cucurbitacin I, or a pharmaceutically acceptable salt or analog thereof), whether administered separately, or as a pharmaceutical composition, can include various other components as additives. Examples of acceptable components or adjuncts which can be employed in relevant circumstances include antioxidants, free radical scavenging agents, peptides, growth factors, antibiotics, bacteriostatic agents, immunosuppressives, anticoagulants, buffering agents, anti-inflammatory agents, anti-pyretics, time-release binders, anesthetics, steroids, and corticosteroids. Such components can provide additional therapeutic benefit, act to affect the therapeutic action of the cucurbitacin compound, or act towards preventing any potential side effects which may be posed as a result of administration of the cucurbitacin compound. The cucurbitacin compounds of the subject invention can be conjugated to a therapeutic agent, as well.

Additional agents that can co-administered to a patient in the same or as a separate formulation include those that modify a given biological response, such as immunomodulators. For example, proteins such as tumor necrosis factor (TNF), interferon (such as alpha-interferon and beta-interferon), nerve growth factor (NGF), platelet derived growth factor (PDGF), and tissue plasminogen activator can be administered. Biological response modifiers, such as lymphokines, interleukins (such as interleukin-1 (IL-1), interleukin-2 (IL-2), and interleukin-6 (IL-6)), granulocyte macrophage colony stimulating factor (GM-CSF), granulocyte colony stimulating factor (G-CSF), or other growth factors can be administered.

The subject invention also provides an article of manufacture useful in treating cancer characterized by constitutive activation of the JAK and/or STAT signaling pathways. The article contains a pharmaceutical composition containing cucurbitacin I, or a pharmaceutically acceptable salt or analog thereof, and a pharmaceutically acceptable carrier or diluent. The article of manufacture can be, for example, a vial, bottle, intravenous bag, syringe, nasal applicator, microdialysis probe, or other container for the pharmaceutical composition. The nasal applicator containing the pharmaceutical composition of the invention can further comprise a propellent. The article of manufacture can further comprise packaging. The article of manufacture can also include printed material disclosing instructions for concerning administration of the pharmaceutical composition for the treatment of cancer. Preferably, the printed material discloses instructions concerning administration of the pharmaceutical composition for the treatment of cancer characterized by constitutive activation of the JAK/STAT signaling pathway. The printed material can be embossed or imprinted on the article of manufacture and indicate the amount or concentration of the active agent (cucurbitacin I or an analog thereof), recommended doses for treatment of the cancer, or recommended weights of individuals to be treated.

In a further aspect, the subject invention concerns a method of screening substances for antitumor activity using a phosphotyrosine-STAT3-specific cytoblot. Using the method of the present invention, modulation of STAT3 can be utilized to evaluate the antitumor efficacy of a candidate substance on a broad spectrum of cancer cells and cell lines.

In one embodiment, the screening method of the subject invention is a phosphotyrosine STAT3-specific cytoblot that has allowed the identification of the compounds described herein that exhibit JAK/STAT3 signaling inhibitory activity. JSI-124 blocked activation of STAT3 in several human cancer cell lines that contain high levels of constitutively-activated tyrosine phosphorylated STAT3 and subsequently inhibited STAT3 DNA-binding activity and STAT3-dependent gene expression. This JAK/STAT3 signaling disrupter is highly selective in that other oncogenic and tumor survival pathways were not affected. The ability of JSI-124 to increase mouse survival and to inhibit growth in mice of human and murine tumors and oncogene-transformed NIH 3T3 tumors with high levels of constitutively-activated STAT3 but not the growth of those with low levels of activated STAT3 further validates interfering with STAT3 signaling as a sound approach to cancer chemotherapy. Present studies are geared towards evaluating the antitumor efficacy of JSI-124 in a broader spectrum of human cancer cell lines and towards identifying the biochemical target of JSI-124.

The screening method of the subject invention involves applying cells to a substrate, such as a tissue culture plate defining one or more receptacles (wells) for containing the cells; contacting one or more candidate substances with the cells; permeabilizing the cells; adding a ligand specific for STAT3 protein (preferably, for phosphotyrosine-STAT3 protein), wherein the ligand contains or is associated with a detectable label; and detecting the label, thereby detecting phospho-STAT3 protein within the cells. Optionally, the method can include the step of removing or otherwise segregating any labeled ligand that has not bound to, or become associated with, phospho-STAT3. The detectable label can be directly attached to the phospho-STAT3 specific ligand or indirectly attached to the ligand through an intermediate entity. Optionally, the method can further include the step of quantifying the amount of STAT3 protein in the cells. The steps of the method of the invention can be carried out in any appropriate order that permits detection of phospho-STAT3.

The substrate can be a solid support or matrix, such as a membrane. The substrate can be porous, semi-porous, or non-porous. Exemplary materials for the substrate include those utilized for the cytoblot described in Materials and Methods, as well as latex, cellulose, nitrocellulose, and nylon. Other examples of suitable substrate materials include polyvinylidinedifluoride (PVDF) and other polyvinyl materials.

Preferably, the ligand specific for phospho-STAT3 is a primary antibody (monoclonal or polyclonal). The primary antibody can be bound or otherwise associated with the intermediate entity, such as a secondary antibody. The secondary antibody can be conjugated to a detectable label, such as horseradish peroxidase. Preferably, the detectable label is detected by Western blot, such as a Western blot chemiluminescence assay. The amount of detected label (and hence detected phosphotyrosine-STAT3) can be determined or quantified using densitometry, for example.

As used herein, the term "antibody" refers to immunoglobulin molecules and immunologically active portions of immunoglobulin molecules, such as molecules that contain an antigen binding site which specifically binds (immunoreacts with) an antigen, such as phosphorylated STAT3. Examples of immunologically active portions of immunoglobulin molecules include F(ab) and F(ab')$_2$ fragments which can be generated by treating the antibody with an enzyme such as pepsin.

The detectable label can operate through any of a variety of mechanisms, permitting detection through fluorescent, luminescent, and/or enzymatic properties, for example.

Cells can be permeabilized sufficiently to allow exposure of the phospho-STAT3 ligand to phospho-STAT3 using methods and agents known to those of ordinary skill in the art. For example, an appropriate solvent, such as methanol, can be applied to the cells.

The cells applied to the substrate can be any type of cell, such as fibroblasts, and are preferably cancer cells of a tumor cell line. Exemplified cancer cells are disclosed herein. The cancer cells can be genetically engineered to contain an oncogene, such as src, or artificially induced to become transformed, such as by exposure to a carcinogen. Preferably, the cells applied to the substrate are cancer cells, wherein the cancer is of a form characterized by constitutive activation of the JAK2 and/or STAT 3 signaling pathways. Preferably, the cells are whole or intact cells.

Preferred cells (transformed cells or non-transformed cells) include, for example, neurons, fibroblasts smooth muscle cells, cardiac cells, skeletal muscle cells, glial cells, embryonic stem cells, adult stem cells, mast cells, adipocytes, protozoans, bacterial cells, yeast cells, and immune cells. The cells can be vertebrate cells, including mammalian cells, such as human or non-human mammal cells. Preferably, the cells applied to the substrate are selected from the group consisting of human cells, mouse cells, rat cells, and rabbit cells.

The quantity of phosphotyrosine-STAT3 detected in the cells contacted with the candidate substance can be compared to known amounts of phosphotyrosine-STAT3 in other cells. For example, where candidate substances are screened by exposing cancer cells to the candidate substances, the quantity of phosphotyrosine-STAT3 detected in the cancer cells exposed to the candidate substance can be compared to a known quantity of phosphotyrosine-STAT3 detected in cancer cells that have not been exposed to the candidate substance. Further, a control step can be conducted where the quantity of phosphotyrosine-STAT3 detected in the cancer cells exposed to the candidate substance is compared to the quantity of phosphotyrosine-STAT3 detected in a corresponding normal (non-cancer) cell, where the normal cell has or has not been exposed to the candidate agent. Comparisons of phosphotyrosine-STAT3 quantities are preferably carried out using cells of the same type, such as fibroblasts.

Preferred substances that are tested according to the screening method of the subject invention include a variety of entities, such as organic compounds, including small molecules; lipids; carbohydrates; peptides; peptidomimetics; inorganic compounds; nucleic acids, such as DNA and RNA molecules); and ions, such as metal ions. Various treatments, such as radiation treatments can be applied to the test cells, as well.

Using the screening method of the subject invention, a plurality of candidate substances, at various concentrations, can be screened simultaneously on a variety of different types of cells at various concentrations. For example, samples of various cells can be seeded into specific wells of a substrate or solid support, such as an assay plate, and a variety of substances can be contacted to the cells, as a combination-type array. Mixtures of two or more substances can also be applied to a single sample of cells, or multiple samples of cells.

In another aspect, the subject invention concerns substances identified as inhibitors of the STAT3 signaling pathway using the screening methods disclosed herein.

In another aspect, the subject invention concerns a kit for screening one or more substances for antitumor activity. The kit of the subject invention can include a ligand specific for phosphotyrosine-STAT3 protein, wherein the ligand is directly or indirectly associated with a detectable label; and at least one of the following: cells for screening the candidate substance(s) for phosphotyrosine-STAT3 inhibitory activity; and a substrate for applying the cells, as described with respect to the screening method of the subject invention.

As used herein, the term "apoptosis", or programmed cell death, refers to the process in which the cell undergoes a series of molecular events leading to some or all of the following morphological changes: DNA fragmentation; chromatin condensation; nuclear envelope breakdown; and cell shrinkage.

As used herein, the term "STAT" refers to signal transducers and activators of transcription, which represent a family of proteins that, when activated by protein tyrosine kinases in the cytoplasm of the cell, migrate to the nucleus and activate gene transcription. Examples of mammalian STATs include STAT1, STAT2, STAT3, STAT4, STAT5a, STAT5b, and STAT6.

As used herein, the term "JAK" refers to a member of a family of non-receptor tyrosine kinases that transfers a phosphate moiety to tyrosine on recipient proteins. Examples include JAK1 and JAK2.

As used herein, the term "signaling" and "signaling transduction" represents the biochemical process involving transmission of extracellular stimuli, via cell surface receptors through a specific and sequential series of molecules, to genes in the nucleus resulting in specific cellular responses to the stimuli.

As used herein, the term "constitutive activation," as in the constitutive activation of the STAT pathway, refers to a condition where there is an abnormally elevated level of tyrosine phosphorylated STAT3 within a given cancer cell(s), as compared to a corresponding normal (non-cancer or non-transformed) cell. Constitutive activation of STAT3 has been exhibited in a large variety of malignancies, including, for example, breast carcinoma cell lines; primary breast tumor specimens; ovarian cancer cell lines and tumors; multiple myeloma tumor specimens; blood malignancies, such as acute myelogenous leukemia; and breast carcinoma cells, as described in published PCT international application WO 00/44774 (Jove, R. et al.), the disclosure of which is incorporated herein by reference in its entirety.

All patents, patent applications, provisional applications, and publications referred to or cited herein are incorporated by reference in their entirety, including all figures and tables, to the extent they are not inconsistent with the explicit teachings of this specification.

MATERIALS AND METHODS

Cell Lines. All human and murine tumor cell lines used were obtained from American Type Culture Collection, Manassas, Va. Stably transfected v-Src, oncogenic H-Ras, and vector NIH 3T3 cell lines have been described previously (Turkson, J. et al. *Mol. Cell Biol.*, 1999, 19:7519-7528; Lerner, E. C. et al. *J. Biol. Chem.*, 1995, 270:26802-26806).

Cytoblot Screening for Phospho-STAT3 Inhibition. NIH 3T3 cells stably transfected with v-Src or NIH 3T3 vector control cells (Turkson, J. et al. *Mol. Cell Biol.*, 1999, 19:7519-7528) were plated into sterile, opaque, 96-well tissue culture plates at 25,000 cells/well. After overnight growth at 37° C., the cells were treated for 4 hr in the presence of either vehicle control or 10 μM of NCI Diversity Set compounds (http://dtp.nci.nih.gov/). After treatment, cells were washed in 100 μl cold TBS (10 mM Tris, pH 7.4, 150 mM NaCl), then fixed for one hour at 4° C. with 190 μl per well of cold 3.7% formaldehyde in TBS as described previously (Stockwell, B. R. et al. *Chem. Biol.*, 1999, 6:71-83). Membranes were permeabilized during a five-minute incubation in ice-cold methanol at 4° C. Cells were washed with 180 μl per well 3% milk in TBS then rocked overnight at 4° C. with 50 μl per well of 3% milk in TBS containing 1:1000 dilution of anti-phospho-STAT3 (P-Tyr 705; Cell Signaling Technology, Beverly, Mass.) and 1:2000 dilution of HRP-conjugated goat anti-rabbit IgG (Jackson ImmunoResearch, West Grove, Pa.). Antibodies were aspirated and then plates were washed twice with 180 μl per well TBS. Results were visualized by adding Western blot chemiluminescence reagent directly to the wells of the plates, incubating at room temperature for 5 min, then placing X-ray film directly on top of the plate in a dark room for 1-5 min. Quantification of results was done using GS-700 scanning densitometer (Bio-Rad Laboratories, Hercules, Calif.).

Western Blotting. Treated cell samples were lysed in 30 mM Hepes, pH 7.5, 10 mM NaCl, 5 mM $MgCl_2$, 25 mM NaF, 1 mM EGTA, 1% Triton-X-100, 10% glycerol, 2 mM sodium orthovanadate, 10 μg/ml aprotinin, 10 μg/ml soybean trypsin inhibitor, 25 μg/ml leupeptin, 2 mM PMSF, and 6.4 mg/ml p-nitrophenylphosphate. Phospho-STAT3, phospho-AKT, phospho-MEK, and phospho-p42/p44 MAPK antibodies were obtained from Cell Signaling Technologies, Cambridge, Mass. Antibodies to STAT3, JAK2, and phospho-JNK were purchased from Santa Cruz Biotechnology, Santa Cruz, Calif. Phospho-JAK2 antibody came from Upstate Biotechnology, Lake Placid, N.Y. Membranes were blocked in either 5% milk in PBS, pH 7.4, containing 0.1% Tween-20 (PBS-T) or 1% BSA in TBS, pH 7.5, containing 0.1% Tween-20 (TBS-T). Phospho-specific antibodies (excepting P-MAPK and P-JNK) were incubated in 1% BSA in TBS-T while all other antibodies were diluted in 5% milk in PBS-T for either 2 hr at room temperature or overnight at 4° C. HRP-conjugated secondary antibodies (Jackson ImmunoResearch) were diluted in 5% milk in either PBS-T or TBS-T at 1:1000 dilution for one hour at room temperature. Western blots were visualized using enhanced chemiluminescence as described previously (Blaskovich, M. A. et al. *Nat. Biotechnol.*, 2000, 18:1065-1070).

Immunoprecipitation of STAT3. A549 cells were treated for 4 hr with vehicle or JSI-124, then lysed in 150 mM Hepes, pH 7.5, 150 mM NaCl, 1 mM EDTA, 0.5% Nonidet P-40 (NP-40), 10% glycerol, 5 mM NaF, 1 mM DTT, 1 mM PMSF, 2 mM sodium orthovanadate, and 5 μg/ml leupeptin. Sample lysates were collected and cleared, then 500 μg of lysate was immunoprecipitated with 50 ng STAT3 antibody overnight at 4° C. then rocked with 25 μl Protein A/G PLUS agarose (Santa Cruz Biotechnology) for 1 hr at 4° C. Samples were washed four times with lysis buffer then boiled in 2×SDS-PAGE sample buffer and run on 10% SDS-PAGE gel. Protein was transferred to nitrocellulose and then blotted as above for both phospho-specific STAT3 and STAT3.

DNA Binding and Transcription. The STAT3 reporter, pLucTKS3, driving expression of firefly luciferase has been previously described (Turkson, J. et al. *Mol. Cell Biol.*, 1999, 19:7519-7528). The pLucTKS3 plasmid harbors seven copies of a sequence corresponding to the STAT3-specific binding site in the promoter of the human C-reactive protein gene (Zhang, D. et al. *J. Biol. Chem.*, 1996, 271:9503-9509). The STAT3-independent plasmid, pRLSRE, contains two copies of the serum response element (SRE) from the c-fos promoter (Yamauchi, K. et al. *J. Biol. Chem.*, 1993, 268:14597-14600), subcloned into renilla luciferase reporter, pRL-null (Promega Corporation, Madison, Wis.).

Transfection and Generation of Stable Clones. NIH 3T3/v-Src/pLucTKS3 and NIH 3T3/v-Src/pRLSRE are stable clones that were generated by transfecting NIH 3T3/v-Src fibroblasts with pLucTKS3 or pRLSRE and selecting for G418-resisitant and zeocin clones, respectively (Turkson, J. et al. *Mol. Cell Biol.*, 1999, 19:7519-7528; Turkson, J. et al. *J. Biol. Chem.*, 2001, 28:28). In the case of NIH 3T3/v-Src/pLucTKS3/pRLSRE, pRLSRE was transfected into NIH 3T3/v-Src/pLucTKS3 cells and stable G418-resistant clones were selected. Transfections were carried out with LipofectAMINE Plus (Invitrogen. Corporation, Carlsbad, Calif.) according to the manufacturer's protocol. Treatment of cells with inhibitors: Src-transformed NIH 3T3 cells stably expressing reporter constructs pLucTKS3 or pRLSRE or both were treated with JSI-124 (10 μM) for 24-48 hr prior to harvesting cells for cytosolic and nuclear extracts preparation and luciferase assay.

Preparation of Cytosolic Extracts. Cytosolic extracts were prepared from fibroblasts as previously described (Turkson, J. et al. *Mol. Cell Biol.*, 1999, 19:7519-7528). Briefly, after two washes with PBS and equilibration for 5 min with 0.5 ml of PBS-0.5 mM EDTA, cells were scraped off the dishes and the cell pellet was obtained by centrifugation (4500×g, 2 min, 4° C.). Cells were resuspended in 0.4 ml of low-salt HEPES buffer (10 mM HEPES, pH 7.8, 10 mM KCl, 0.1 mM EGTA, 0.1 mM EDTA, 1 mM PMSF, and 1 mM DTT) for 15 min, lysed by the addition of 20 µl of 10% NP-40, and centrifuged (10,000×g, 30 sec, 4° C.) to obtain the cytosolic supernatant, which was used for luciferase assays (Promega Corporation) measured with a luminometer.

Nuclear Extract Preparation and Gel Shift Assay. Nuclear extract preparation and electrophoretic mobility shift assay were carried out as previously described (Turkson, J. et al. *Mol. Cell Biol.*, 1999, 19:7519-7528). The $^{32}$P-radiolabeled oligonucleotide probe is hSIE (high affinity sis-inducible element, m67 variant, 5'-AGCTICATTICCCGTAAATCCCTA-3') (SEQ ID NO. 1) that binds STAT1 and STAT3.

JAK Kinase Assays. A549, MDA-MB-468, and v-Src transformed NIH 3T3 cells were harvested, washed three times in PBS-V (10 mM sodium phosphate, pH 7.4, 137 mM NaCl, 1 mM sodium orthovanadate) then lysed for 30 min on ice in JAK kinase lysis buffer (25 mM Hepes, pH 7.4, 0.1% Triton-X-100, 0.5 mM DTT, 1 mM sodium orthovanadate, 1 mM PMSF, 10 µg/ml aprotinin, 10 µg/ml leupeptin). Samples were spun at high speed to clear, and 800-1000 µg of protein was immunoprecipitated per treatment condition with 50 ng of either JAK1 or JAK2 antibody (Santa Cruz Biotechnology) rocking overnight at 4° C. 25 µl of protein A/G PLUS agarose then was added and rocking continued for 1 hr at 4° C. Samples were spun to collect agarose pellet, and pellet washed twice in wash buffer (50 mM Hepes, pH 7.4, 0.1% Triton-X-100, 0.5 mM DTT, 150 mM NaCl) and once in phosphorylation buffer (50 mM Hepes, pH 7.4, 0.1% Triton-X-100, 0.5 mM DTI, 6.25 mM manganese chloride, 100 mM NaCl). Kinase reactions were performed at 30° C. for 15 min in a final volume of 100 µl of phosphorylation buffer. Samples were pretreated with DMSO control, JSI-124, and control compounds (AG490, 100 µM, and PD180790, 2 µM) before addition of 20 µCi/sample y-[$^{32}$P]ATP. Reaction was halted using stop buffer (wash buffer plus 10 mM EDTA), samples spun to collect pellet, then pellet washed once with stop buffer and twice with wash buffer. Samples were then placed in 2×SDS-PAGE sample buffer, boiled at 100° C., and run on 8% SDS-PAGE gels to separate proteins. Autophosphorylation results were visualized by autoradiography.

Src Kinase Assay. A549, MDA-MB-468, and v-Src cells were harvested and lysed for 30 min on ice in RIPA150 buffer (10 mM Tris, pH 7.5, 150 mM NaCl, 10% glycerol, 5 mM EDTA, 1% Triton-X-100, 0.1% SDS, 100 µM sodium orthovanadate, 10 µg/ml aprotinin, 10 µg/ml leupeptin, 1 µg/ml antipain). Samples were spun at high speed to clear, then 1000 µg of protein were immunoprecipitated per treatment condition with 2 µg v-Src antibody (Ab-1, Oncogene Research Products, San Diego, Calif.) rocking overnight at 4° C. 25 µl of protein A/G PLUS agarose then was added and rocking continued for 4 hr at 4° C. Samples were spun to collect agarose pellet, and pellet washed three times in RIPA150 buffer, twice in RIPA10 buffer (10 mM Tris, pH 7.5, 10 mM NaCl, 10% glycerol, 5 mM EDTA, 1% Triton-X-100, 0.1% SDS, 100 µM sodium orthovanadate 10 µg/ml aprotinin, 10 µg/ml leupeptin, 1 µg/ml antipain), and three times in 40 mM Tris, pH 7.4. Pellet was then resuspended in 30 µl kinase reaction buffer (20 mM Tris, pH 7.4, 5 mM MgCl$_2$) containing 10 µCi γ-[$^{32}$P]ATP. Inhibitors were preincubated for several minutes before the addition of the ATP. Kinase reactions were carried out at room temperature for 15 min. Reaction was stopped with the addition of 2×SDS-PAGE sample buffer. Samples were boiled and run on 10% SDS-PAGE gels. Autophosphorylation results were visualized by autoradiography.

Antitumor Activity in the Nude Mouse Tumor Xenograft Model. Nude mice and C57 BL-6 black mice (National Cancer Institute, Bethesda, Md.) were maintained in accordance with the Institutional Animal Care and Use Committee (IACUC) procedures and guidelines. v-Src- and oncogenic H-Ras-transformed NIH 3T3, A549, MDA-MB-468 and Calu-1 cells were harvested, resuspended in PBS and injected s.c. into the right and left flank (10×10$^6$ cells per flank) of 8 week old female nude mice as reported previously (Sun, J. et al. *Cancer Res.*, 1999, 59:4919-4926). Similarly, murine B16-F10 Melanoma cells were injected s.c. into the right and left flank (10$^6$ cells per flank) of C57 black mice. When tumors reached about 150 mm$^3$, animals were randomized (five animals per group; two tumors per animal) and dosed i.p. with 0.2 ml once daily. Control animals received DMSO (20%) vehicle whereas treated animals were injected with JSI-124 (1 mg/kg/day) in 20% DMSO in water. The tumor volumes were determined by measuring the length (l) and the width (w) and calculating the volume (V=lw$^2$/2) as described previously (Sun, J. et al. *Cancer Res.*, 1999, 59:4919-4926). Statistical significance between control and treated animals were evaluated by using Student's t-test. For the mouse survival experiments, C57 BL-6 black mice were implanted s.c. with B16-F10 cells (10$^5$ to 10$^6$ cells per flank). On day 5 after implantation the mice were randomized (6 animals per group) and treated with either vehicle or JSI-124 (1 mg/Kg/day) for 25 days. Percent surviving mice was determined by monitoring the death of mice until all mice died. Two experiments of 12 animals each (6 control and 6 treated with JSI-124) were carried out. For statistical analysis: for each of the two experiments, mice receiving JSI-124 were compared to those receiving vehicle control with respect to survival using the permutation log rank test as implemented in the statistical software package, ProcStatXact (p-values are two sided and exact). The results of both experiments were then pooled in a stratified analysis and resulted in a p-value of 0.01.

EXAMPLE 1

Development of Phosphotyrosine STAT3-Specific Cytoblot High Throughput Assay and Identification of JSI-124

Figure 2:
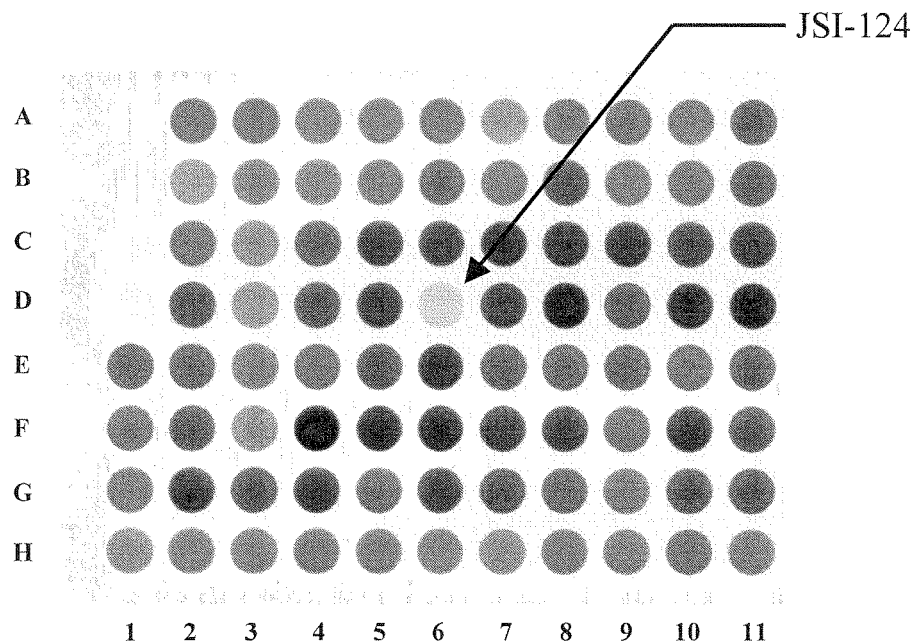
FIG. 2 shows v-Src-transformed NIH 3T3 cells containing constitutively-activated tyrosine phosphorylated STAT3, which were plated in all wells of the 96-well plate except for wells 1A, 1B, 1C and 1D, where NIH 3T3 cells transfected with empty vector were plated. Wells A through H of column 1 were treated for 4 hours with vehicle, whereas all other wells were treated with compounds from the NCI diversity set (each well received a different compound). The cells were then permeabilized and cytoblotted with an anti-phosphotyrosine STAT3-specific antibody as described under Materials and Methods.

STAT3 is found tyrosine phosphorylated and constitutively-activated in many human cancer types. Blockade of this aberrant activation using dominant negative STAT3 was previously shown to result in inhibition of tumor growth and induction of tumor cell apoptosis, giving strong support to the validation of STAT3 as a cancer drug discovery target (reviewed in Bowman, T. et al. *Cancer Control*, 1999, 6:427-435; Turkson, J and R. Jove *Oncogene*, 2000, 19:6613-6626; and Bowman, T. et al. *Oncogene*, 2000, 19:2474-2488). In an attempt to identify novel anticancer drugs based on interfering with the aberrant activation of STAT3, a high throughput cytoblot assay was developed in which the levels of activated tyrosine phosphorylated STAT3 are determined by an antibody specific for tyrosine phosphorylated STAT3. Using this cytoblot assay, a library consisting of 1,992 compounds from the National Cancer Institute (referred to as the NCI Diversity Set) has been screened for agents capable of blocking v-Src activation of STAT3 in NIH 3T3 cells as described under Materials and Methods. Analysis of the cytoblot results indicated that several compounds inhibited activation of STAT3 to various degrees. The most potent of these compounds, JSI-124 (NCI identifier: NSC 521777), suppressed v-Src activated STAT3 at a concentration of 10 µM. FIG. 1 shows the structure of JSI-124 which is also known as cucurbitacin 1 (Witkowski, A. and J. Konopa *Biochim. Biophys. Acta.*, 1981, 674:246-255; Duncan, K. L. et al. *Biochem. Pharmacol.*, 1996, 52:1553-1560; Dinan, L. et al. *Biochem*. 1997, 327: 643-650). FIG. 2 shows an example of a 96-well plate cytoblot where the effects of 88 compounds from the NCI Diversity Set on phosphotyrosine STAT3 levels were evaluated. JSI-124 (10 µM) at position D6 on the plate reduced phosphotyrosine STAT3 to barely detectable levels.

EXAMPLE 2

JSI-124 Suppresses Phosphotyrosine STAT3 Levels in Human Cancer Cell Lines

Figure 3A:
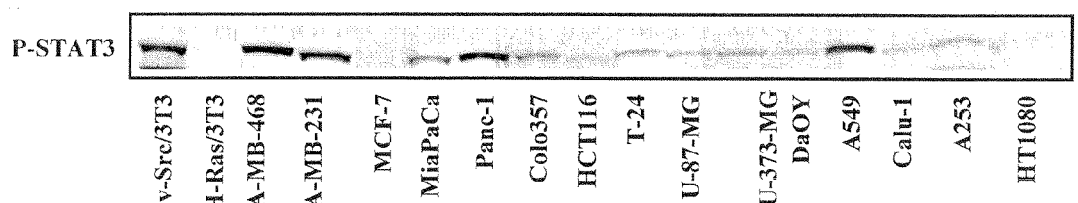
FIGS. 3A-3C suppression of phosphotyrosine STAT3 levels in v-src-transformed NIH 3T3 cells and human cancer cell lines by JSI-124.
Figure 3B:
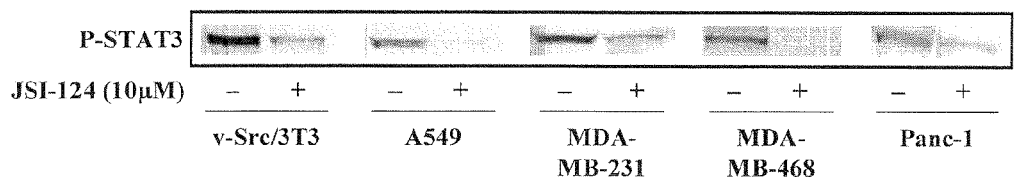

The results of the cytoblot shown in FIG. 2 identifies JSI-124 as an inhibitor of v-Src activation of STAT3 in NIH 3T3 cells. To determine whether JSI-124 suppresses phosphotyrosine STAT3 levels in human cancer cell lines, several human cancer cell lines were evaluated and those with high levels of tyrosine phosphorylated STAT3 were identified, as shown in FIG. 3A. Among the human cancer cell lines evaluated A549 (a lung adenocarcinoma), MDA-MB-468 and MDA-MB-231 (two breast carcinomas), and Panc-1 (a pancreatic carcinoma) contained high levels of tyrosine phosphorylated STAT3. These human cancer cell lines along with the positive control cell line (v-Src transformed NIH 3T3 cells) were treated with either vehicle or JSI-124 (10 µM) for 4 hr and the cell lysates processed for Western blotting with anti-phosphotyrosine STAT3 antibody as described under Methods. FIG. 3B shows that JSI-124 was very effective at reducing the levels of tyrosine phosphorylated STAT3. These results confirm those of the cytoblot and demonstrate the ability of JSI-124 to suppress the levels of constitutively-activated, tyrosine phosphorylated STAT3 not only in v-Src transformed NTH 3T3 murine fibroblasts but also in human cancer cells of epithelial origin.

Figure 3C:
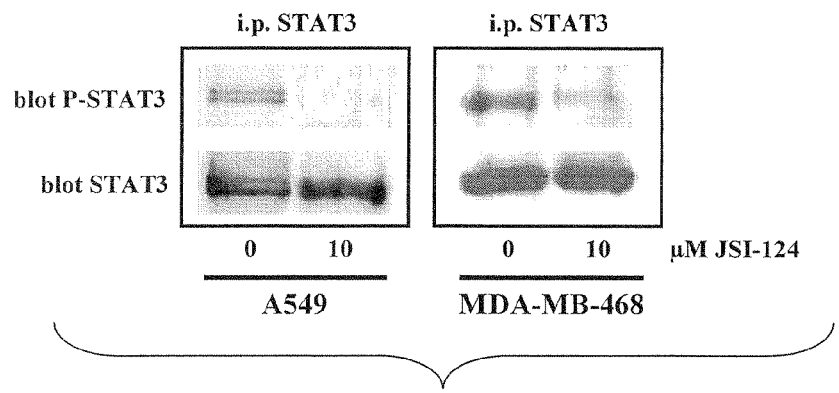

Because the phosphotyrosine STAT3 antibody could possibly cross-react with other tyrosine phosphorylated proteins, the fact that JSI-124 suppresses phosphotyrosine STAT3 levels was confirmed by first immunoprecipitating STAT3 with an anti-STAT3 antibody and then Western blotting with anti-phosphotyrosine STAT3 antibody. FIG. 3C shows that treatment of A549 and MDA-MB-468 cells with JSI-124 (10 µM) for 4 hr reduced phosphotyrosine STAT3 to barely detectable levels. To determine if JSI-124 affected the STAT3 protein levels, reblotting with anti-STAT3 antibody was carried out. FIG. 3C also shows that JSI-124 has no effect on the protein levels of STAT3. Thus, JSI-124 suppresses the phosphotyrosine levels of STAT3 without affecting its protein levels.

EXAMPLE 3

Figure 4A:
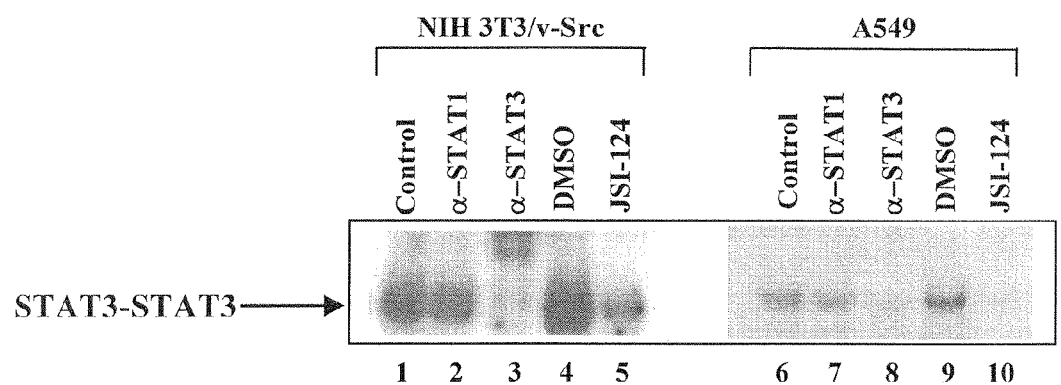
FIGS. 4A and 4B show inhibition of STAT3 DNA-binding activity and STAT3-mediated transcription by JSI-124.

JSI-124 Inhibits STAT3 Signaling by Disrupting STAT3 DNA-binding Activity and STAT3-mediated Gene Expression Tyrosine phosphorylation of STAT3 is required for its biological activity (reviewed in Stark, G. R. et al. *Annu. Rev. Biochem.*, 1998, 67:227-264; Horvath, C. M. and J. E. Darnell *Curr. Opin. Cell. Biol.*, 1997, 9:233-239, Ihle, J. N. and I. M. Kerr *Trends Genet.*, 1995, 11:69-74; Schindler, C. and J. E. Darnell *Annu. Rev. Biochem.*, 1995, 64:621-651). It was reasoned that the suppression by JSI-124 of the phosphotyrosine levels of STAT3 should lead to disruption of STAT3 DNA-binding activity and STAT3-mediated gene expression. To this end, the effect of JSI-124 on STAT3 DNA-binding activity was first evaluated by electrophoretic mobility shift assay (EMSA). v-Src transformed NIH 3T3 cells and A549 cells were treated with vehicle or JSI-124 and nuclear extracts containing activated STAT3 were incubated with [$^{32}$P]-labeled hSIE oligonucleotide probe for EMSA as described under Methods. FIG. 4A shows that STAT3 DNA-binding activity was greatly reduced in nuclear extracts from v-Src/NIH 3T3 and A549 cells treated with JSI-124 compared to extracts from vehicle-treated cells (lanes 4 vs. 5 and 9 vs. 10). To confirm that the band seen in the gel contains STAT3-DNA complexes, the nuclear extracts were preincubated with anti-STAT3 or anti-STAT1 antibodies. The anti-STAT3 but not anti-STAT1 antibody supershifted or blocked the complex demonstrating the protein-DNA complex contains STAT3, not STAT1 (as shown in FIG. 4A, lanes 1,2, and 3 and 6,7, and 8). These results demonstrate that BI-124, by reducing the levels of tyrosine phosphorylated STAT3, inhibits STAT3 signaling resulting in disruption of STAT3 DNA-binding.

Figure 4B:
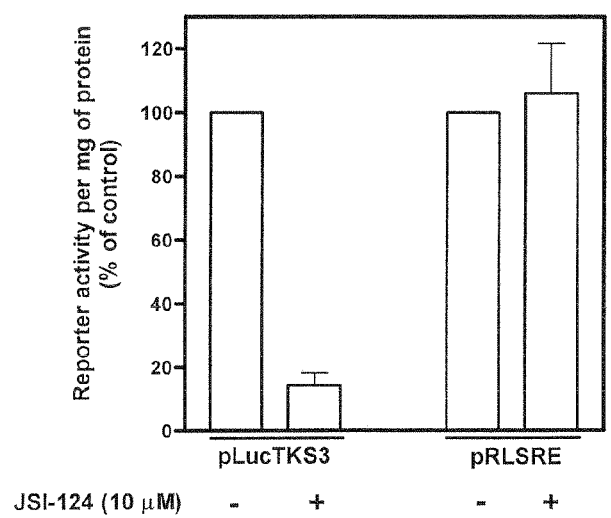

It was next determined if this suppression of STAT3 activation results in inhibition of STAT3-mediated gene expression. To this end, v-Src/NIH 3T3 fibroblasts that stably express a STAT3-dependent firefly luciferase reporter (pLucTKS3) or that stably express a serum response element (SRE)-dependent renilla luciferase reporter (pRLSRE) were treated with either vehicle or JSI-124 and cytosolic extracts prepared for luciferase assays as described under Methods. FIG. 4B shows that JSI-124 significantly suppresses induction of the STAT3-dependent pLucTKS3 luciferase reporter without affecting the pRLSRE reporter. Because in v-Src transformed NIH 3T3 cells, v-Src activates pLucTKS3 in a STAT3-dependent manner and pRLSRE in a STAT3-independent manner, the results shown in FIG. 4B demonstrate that JSI-124 is specific to STAT3-mediated transcription. Thus, JSI-124 inhibits STAT3 signaling by suppressing phosphotyrosine levels of STAT3, inhibiting STAT3-DNA binding and STAT3-mediated gene expression.

EXAMPLE 4

JSI-124 Suppresses Phosphotyrosine Levels of STAT3 and JAK2 but not Src in A549 and MDA-MB-468 Cells The ability of JSI-124 to suppress phosphotyrosine levels of STAT3 suggests that this agent may interfere with the function of the upstream tyrosine kinases JAK and Src that are known to phosphorylate STAT3. The effects of JSI-124 on the phosphotyrosine levels of JAK2 and Src in whole cells as well as the ability of JSI-124 to inhibit Src, JAK1, and JAK2 kinase activities in vitro were evaluated. FIG. 5A shows that treatment of A549 and MDA-MB-468 with JSI-124 results in reduction of the levels of tyrosine phosphorylated STAT3, with A549 cells being more sensitive than MDA-MB-468. Furthermore, JSI-124 was also effective at suppressing the levels of tyrosine phosphorylated JAK2 but not those of tyrosine phosphorylated Src. JSI-124 had no effect on the protein levels of STAT3 and JAK2 in both cell lines, as shown in FIG. 5A.

The effects of JSI-124 on JAK/STAT3 signaling described above were determined after 4 hr of JSI-124 treatment. To ascertain the length of treatment time required for JSI-124 to suppress phosphotyrosine STAT3 and JAK levels, a time course experiment was carried out. FIG. 5B shows that treatment of A549 and MDA-MB-468 cells with JSI-124 for as little as 60 min was effective, and in both cell lines the suppression was complete by 2 hr. Thus, the suppression by JSI-124 of the levels of tyrosine phosphorylated STAT3 and JAK2 is rapid.

The ability of JSI-124 to inhibit the kinase activities of Src, JAK1, and JAK2 in vitro was next evaluated. To this end, Src, JAK1, and JAK2 were immunoprecipitated from either A549, MDA-MB-468, or v-Src/NIH 3T3 cells and incubated the immunoprecipitates with either vehicle control, JSI-124, the JAK tyrosine kinase inhibitor AG490, or the Src kinase inhibitor PD180970 and followed autophosphorylation of Src, JAK1, and JAK2 as described under Methods. FIG. 5C shows that in all three cell lines as expected PD180970 inhibits Src but not JAK1 or JAK2 activities (A549 did not have JAK1 kinase activity). Similarly, AG490 inhibited JAK1 and JAK2 but not Src kinase activities. In contrast, all three kinase activities were not affected by JSI-124, as shown in FIG. 5C. Therefore, although in whole cells JSI-124 is very effective at suppressing the levels of tyrosine phosphorylated STAT3 and JAK2, it is unable to inhibit directly Src, JAK1, or JAK2 kinase activities in vitro.

EXAMPLE 5

Figure 6:
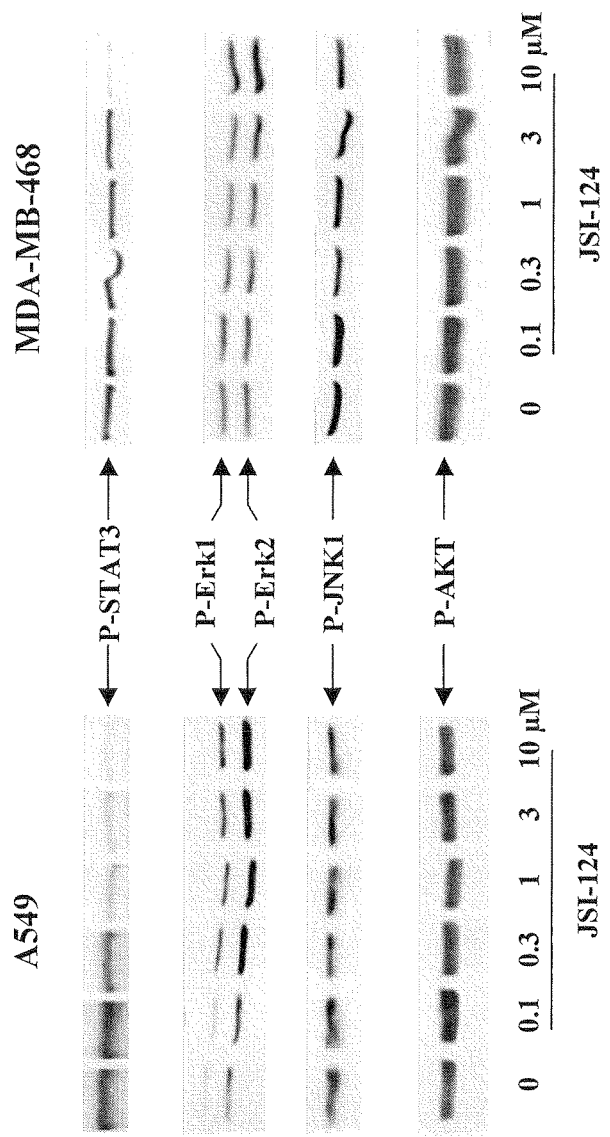
FIG. 6A and 6B show suppression by JSI-124 of phosphorylation levels of STAT3, but not Erk1/Erk2, JNK and Akt. A549 and MDA-MB-468 were treated with various concentrations of JSI-124 (0-10 µM) and processed for immunoblotting with phospho-specific antibody against either STAT3, Erk1, Erk2, JNK or Akt as described under Methods. Data are representative of three independent experiments.

JSI-124 is Highly Selective for the JAK/STAT3 over Akt, Erk, and JNK Signaling Pathways To determine whether the effects of JSI-124 were selective to the JAK/STAT3 pathway over other oncogenic and survival pathways, A549 and MDA-MB-468 cells were treated with various concentrations of JSI-124 and processed the lysates for Western blotting with antibodies specific for phospho-STAT3, phospho-Erk1/2, phospho-JNK, and phospho-Akt as described under Methods. FIG. 6 shows that A549 and MDA-MB-468 have constitutively phosphorylated Erk1 /Erk2, ,TNK1, and Akt in addition to phospho-STAT3. Treatment with JSI-124 resulted in suppression of phospho-STAT3 levels in both cell lines. In contrast, treatment with JSI-124 had no inhibitory effect on phospho-Akt, phospho-Erk1/2, or phospho-JNK with a concentration as high as 10 µM. With Erk1/2, not only did JSI-124 not inhibit but actually it increased the levels of phosphorylation. Thus, these results demonstrate that JSI-124 suppressive effects are highly selective for the JAK/STAT3 over Erk, JNK, and Akt tumor survival and oncogenic signaling pathways.

EXAMPLE 6

JSI-124 Inhibits Growth in Mice of Tumors with High Levels of Constitutively-activated STAT3

Previous studies have shown that interfering with STAT3 signaling using a gene therapy approach with a dominant negative variant of STAT3 (STAT3-13) resulted in inhibition of the growth of melanoma cells in nude mice (Niu, G. et al. *Cancer Res.*, 1999, 59:5059-5063; Catlett-Falcone, R. et al. *Immunity*, 1999, 10:105-115). Because JSI-124 inhibits aberrantly activated STAT3 signaling, DNA binding, and STAT3-mediated gene expression, it was reasoned that the growth in nude mice of tumors with constitutively-activated STAT3 should be more sensitive to JSI-124 than that of tumors with low or without constitutively-activated STAT3. To this end, A549 and MDA-MB-468 as well as Calu-1 cells, a lung adenocarcinoma which has barely detectable levels of tyrosine phosphorylated STAT3 (FIG. 3A), were implanted subcutaneously in nude mice. When the tumors reached an average size of about 150 mm³, the animals were randomized and treated intraperitoneally with either vehicle or JSI-124 (1 mg/kg/day) as described under Methods. FIGS. 7B and 7C, respectively, show that A549 and Calu-1 tumors from animals treated with vehicle grew to about 500 mm³ twenty-six days after tumor implantation. MDA-MB-468 treated with vehicle control grew to about 300 mm³ sixty days after tumor implantation, as shown in FIG. 7A. FIGS. 7B and 7A show that JSI-124 inhibited A549 and MDA-MB-468 tumor growth by 76% and 86%, respectively. In contrast, JSI-124 had little effect on the growth in nude mice of Calu-1 cells, as shown in FIG. 7C. Treatment of mice bearing A549 cells with a reduced dose of 0.5 mg/kg/day for 23 days also inhibited tumor growth by 52% (data not shown). At both doses, 1 mg/kg/day and 0.5 mg/kg/day, JSI-124 had no effects on body weight, activity or food intake of mice. However, at the local site of drug injection, the peritoneal cavity, JSI-124 at the 1 mg/kg/day dose, caused edema. A similar observation was made by the National Cancer Institute Developmental Therapeutics Program where edema was observed at the subcutaneous site of injection (Jill Johnson, NCI, personal communication).

The results from A549, Calu-1, and MDA-MB-468 xenograft studies suggest that human cancer cells which express constitutively-activated. STAT3 should be sensitive to JSI-124. It was further reasoned that if the ability of JSI-124 to inhibit tumor growth in nude mice depends on consti-tutively-activated STAT3, v-Src-transformed NIH 3T3 cells which require constitutively-activated STAT3 for malignant transformation (Yu, C. L. et al. *Science*, 1995, 269:81-83) should be sensitive to JSI-124 whereas oncogenic Ras-transformed NIH 3T3 cells, where STAT3 is not constitutively-activated (see FIG. 3A), should be resistant. FIGS. 7D and 7F show that, in the absence of JSI-124, the growth of both v-Src- and Ras-transformed NIH 3T3 tumors was highly aggressive and reached average sizes of about 2500 mm³ and 1000 mm³, respectively, within 9 days of tumor cell implantation. FIG. 7D also shows that JSI-124 (1 mg/kg/day) inhibited the growth of v-Src/NIH 313 tumors by 64%. In contrast, the growth of Ras/NIH 3T3 tumors was resistant to JSI-124, as shown in FIG. 7F. These results coupled with those from the human tumor xenografts show that JSI-124 selectively targets tumors with constitutively-activated STAT3 signaling.

The above results were obtained from experiments with immune-deficient nude mice. Furthermore, the studies did not investigate the effects of JSI-124 on the survival of mice bearing death-inducing tumors. Therefore, the ability of JSI-124 to inhibit tumor growth and increase survival of immunologically-competent C57 black mice s.c. implanted with the murine B16-F10 melanoma that expresses constitutively activated STAT3 (Niu, G. et al. *Cancer Res.*, 1999, 59:5059-5063) was evaluated. FIG. 6 shows that B16-F10 tumors from control mice injected with vehicle grew to an average size of 1194±141 whereas those treated with JSI-124 (1 mg/Kg/day) grew only to an average size of 588±94. Thus, JSI-124 treatment inhibited tumor growth by 56%. To determine the effect of JSI-124 on mouse survival, s.c. B16-F10 melanoma was implanted and mice survival was followed over time. FIG. 6 shows that mice treated with vehicle begin to die on day 19 after B16-F10 implantation. By day 21, half of the mice were dead, and by day 35 all 6 mice were dead. In contrast, none of the JSI-124-treated mice were dead by day 23, half of the mice died on day 34 and all the mice died by day 42. FIG. 6 also shows that 50% of vehicle-treated mice survived up until day 21 ($T_{50}$=21) whereas the JSI-124-treated group of mice had a longer $T_{50}$ of 34 days. Thus, treatment with JSI-124 significantly increased the life span ($T_{50}$ increase of 13 days) of immunologically-competent mice implanted with B16-F10 melanoma.

EXAMPLE 7

Cucurbitacin Analogs

Figure 15:
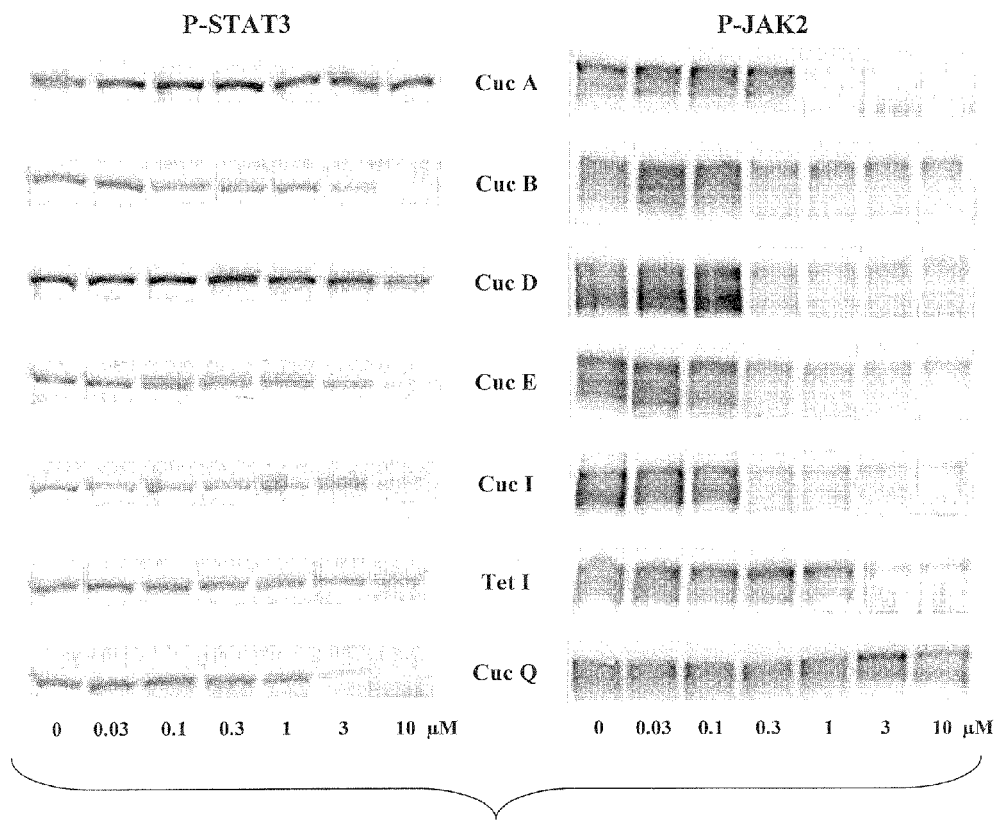
FIG. 15 shows representative blots of the effects of cucurbitacins A, B, D, E, I, Tetrahydro-I, and Q (0 µM-10 µM) on the levels of phospho STAT3 and phospho JAK2 in A-549 cells.

The identification from the NCI diversity set of cucurbitacin I (JSI-124) as a potent ($IC_{50}$=200nM) suppressor of the JAK/STAT3 tumor survival pathway with potent antitumor activity. Structure-activity relationship studies were then carried out in order to identify further antitumor agents representing analogs of cucurbitacin I. To this end, 6 analogs of cucurbitacin I were received from NCI and their ability to inhibit the levels of phosphotyrosine JAK2 and phosphotyrosine STAT3 in the human lung carcinoma cell line A-549 were evaluated by Western blotting as described in Materials and Methods with respect to cucurbitacin I. FIG. 15 shows representative blots of the effects of cucurbitacins A, B, D, E, I, Tet I and Q (0-10 μM) on the levels of phospho STAT3 and phospho JAK2 in A-549 cells. FIG. 17 shows the average and standard deviation of at least three independent experiments for each cucurbitacin molecule tested. From the SAR studies, the following conclusions were made.

Comparing cucurbitacin I to cucurbitacin E (the structures of which are shown in FIG. 1 and FIG. 12, respectively) reveals that a hydroxyl group of cucurbitacin I is important for phosphotyrosine-STAT3 but not phosphotyrosine-JAK2 activity, as its replacement with an acetyl group resulted in a four-fold loss of activity against phospho-STAT3 without affecting activity against JAK2 ($IC_{50}$ for phospho-STAT3, 200 nM for I; 800 nM for E; $IC_{50}$ for phospho-JAK2, 200 nM for I; 200 nM for E).

Comparing cucurbitacin B and cucurbitacin E (shown in FIG. 10 and FIG. 12, respectively) shows that reducing a carbon-carbon double bond results in an additional five-fold loss of inhibitory activity against phosphotyrosine-STAT3, and no reduction in activity against phosphotyrosine-JAK2 ($IC_{50}$ for phospho-STAT3, 4 μM for B; $IC_{50}$ for JAK2, 200 nM for B).

Conversion of a carbonyl group in cucurbitacin B (shown in FIG. 10) to a hydroxyl, as in cucurbitacin Q (shown in FIG. 13), results in additional loss of activity against JAK2 activation, with 2-fold gain in activity against STAT3 activation ($IC_{50}$ for phospho-STAT3, 2 μM for Q; $IC_{50}$ for phospho-JAK2, >10 μM for Q).

The addition of a hydroxyl group in cucurbitacin B (shown in FIG. 10) to get cucurbitacin A (shown in FIG. 9) results in a loss of activity against phosphotyrosine-STAT3 activity, as well as a decrease of the ability of the compound to inhibit phosphotyrosine JAK2 (IC50 for phospho-STAT3, >10 μM for A; IC50 for phospho-JAK2, 1 μM).

Replacement of an acetate in cucurbitacin B (shown in FIG. 10) by a hydroxyl yields cucurbitacin ID (shown in FIG. 11) and reduces activity against phospho STAT3 by 2-fold with no effects on phospho JAK2.

Reduction of two double bonds in cucurbitacin I (shown in FIG. 1) yields tetrahydro cucurbitacin (shown in FIG. 14) and results in reduction of activity against phospho-STAT3 and phospho JAK2.

Figure 16A:
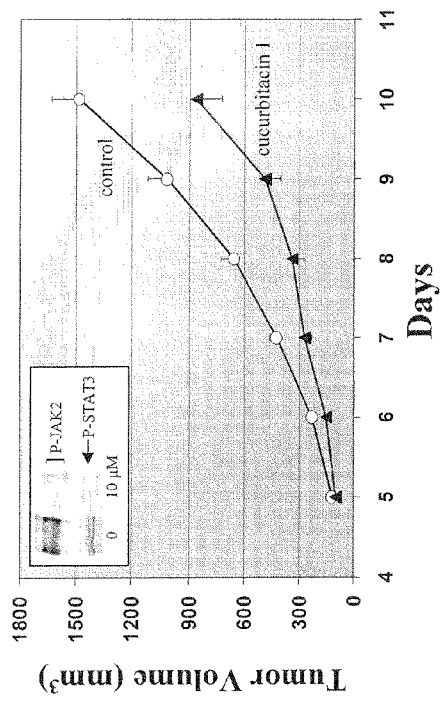
FIGS. 16A-16C compare the ability of the cucurbitacin analogs to inhibit phospho STAT3 or phospho JAK2 levels to their ability to inhibit tumor growth in nude mice.
Figure 16C:
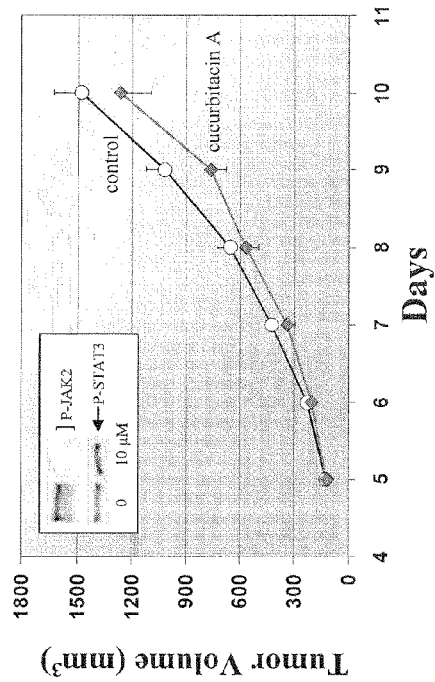
Figure 16B:
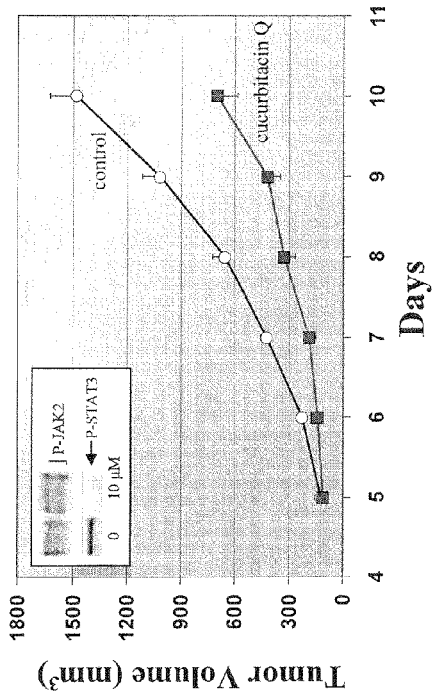

The ability of the cucurbitacin analogs (at 1 mg/Kg/day intraperitonealy) to inhibit the growth of v-src transformed NIH 3T3 cells implanted subcutaneously in nude mice was evaluated, as described with respect to cucurbitacin I. FIG. 17 shows that cucurbitacin Q, tetrahydro-cucurbitacin I, cucurbitacin I, and cucurbitacin E, each inhibit tumor growth. Cucurbitacin A inhibited tumor growth to a lesser extent (16%). Cucurbitacin B was toxic at 1 mpk. However, at 0.2 mpk/day, cucurbitacin B was not toxic and inhibited tumor growth by 40%. Next, the ability of the analogs to inhibit phospho STAT3 or phospho JAK2 levels was correlated to their ability to inhibit tumor growth in nude mice. FIG. 16 shows that cucurbitacin I, which inhibits both phospho STAT3 and phospho JAK2 levels (see inset), inhibit tumor growth. In contrast, cucurbitacin A, which inhibit only phospho JAK2 but not phospho STAT3 levels (see inset), did not significantly inhibit tumor growth. Furthermore, cucurbitacin Q, which inhibits phospho STAT3 but not phospho JAK2 levels (see inset), was as potent as curcubatacin I at inhibiting tumor growth. These results indicate that a cucurbitacin with the ability to inhibit STAT3 activation alone (cucurbitacin Q) is sufficient to inhibit tumor growth. However, cucurbitacin A, which inhibits only JAK2 activation, inhibits tumor growth to a lesser extent. Also, the ability of cucurbitacin I to inhibit both JAK2 and STAT3 activation does not make it a better inhibitor of tumor growth than the cucurbitacin that inhibits STAT3 alone. This indicates that, in a model where both JAK2 and STAT3 are actively signaling cells to grow and survive, it may be more important to shut down the constitutive signaling of STAT3.

It should be understood that the examples and embodiments described herein are for illustrative purposes only and that various modifications or changes in light thereof will be suggested to persons skilled in the art and are to be included within the spirit and purview of this application.

---

We claim:

1. A method for treating non-small cell lung cancer comprising administering cucurbitacin I, or a pharmaceutically acceptable salt or analog thereof, or a composition comprising cucurbitacin I, or a pharmaceutically acceptable salt or analog thereof, to a patient in need of such treatment.

2. The method according to claim 1, wherein the analog is selected from the group consisting of cucurbitacin A, cucurbitacin B, cucurbitacin D, cucurbitacin E, cucurbitacin Q, and tetrahydro-cucurbitacin I.

3. The method according to claim 1, wherein the analog inhibits STAT3 signaling pathway, but does not inhibit JAK2 signaling pathway.

4. The method according to claim 1, wherein the cucurbitacin I, or a pharmaceutically acceptable salt or analog thereof, inhibits STAT3 signaling pathway.

5. The method according to claim 1, wherein the cancer is characterized by abnormal STAT3 pathway activity.

6. The method according to claim 1, wherein the cancer is characterized by abnormal JAK2 pathway activity and abnormal STAT3 pathway activity.

7. The method according to claim 1, wherein cucurbitacin I, or a pharmaceutically acceptable salt thereof, is administered to the patient.

8. The method according to claim 1, wherein route of said administration is selected from the group consisting of intravenous, intramuscular, oral, and intra-nasal.

9. The method according to claim 1, wherein the patient is suffering from a tumor and the cucurbitacin I, or the pharmaceutically acceptable salt or analog thereof, inhibits growth of the tumor.

10. The method according to claim 1, wherein the analog is cucurbitacin Q having the chemical structure:

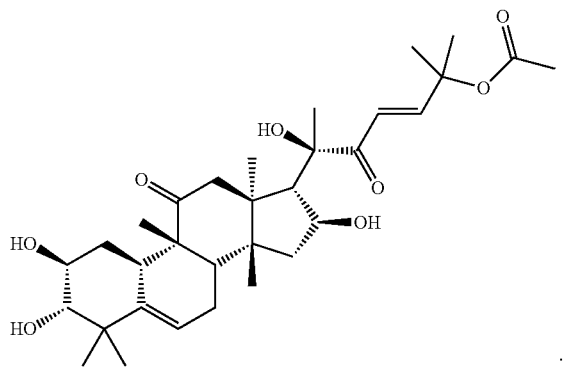

11. The method according to claim 1, wherein the cancer is characterized by constitutive activity of STAT3 signaling pathway.

12. The method according to claim 1, wherein the cancer is characterized by constitutive activation of both JAK2 and STAT3 signaling pathways.

13. The method according to claim 1, wherein the non-small cell lung cancer is an adenocarcinoma.

14. The method according to claim 1, wherein cucurbitacin I, or a pharmaceutically acceptable salt or analog thereof, or a composition comprising cucurbitacin I, or a pharmaceutically acceptable salt or analog thereof, is administered in conjunction with chemotherapy to treat the cancer.

15. The method according to claim 1, wherein the analog is cucurbitacin A.

16. The method according to claim 1, wherein the analog is cucurbitacin B.

17. The method according to claim 1, wherein the analog is cucurbitacin D.

18. The method according to claim 1, wherein the analog is cucurbitacin E.

19. The method according to claim 1, wherein the analog is tetrahydro-cucurbitacin I.

* * * * *

UNITED STATES PATENT AND TRADEMARK OFFICE
CERTIFICATE OF CORRECTION

PATENT NO. : 8,691,799 B2
APPLICATION NO. : 13/209937
DATED : April 8, 2014
INVENTOR(S) : Said M. Sebti and Richard Jove It is certified that error appears in the above-identified patent and that said Letters Patent is hereby corrected as shown below:

In the Specification

Column 1,
Line 64, "Ihie" should read --Ihle--

Column 2,
Lines 11-12, "Bowman, I. *et al.*" should read --Bowman, T. *et al.*--
Line 44, "P13K" should read --PI3K--
Line 56, "o STAT3" should read --of STAT3--

Column 5,
Line 30, "Ste kinase inhibitor PD 180970" should read --Src kinase inhibitor PD180970--

Column 6,
Line 3, "structure 1" should read --structure 1--

Column 9,
Line 22, "tent-butyl" should read --tert-butyl--

Column 16,
Line 2, "phospho-INK" should read --phospho-JNK--

Column 17,
Line 11, "AGCTICATTICCCGTAAATCCCTA"
        should read
    --AGCTTCATTTCCCGTAAATCCCTA--

Column 17,
Line 29, "0.5 mM DTI" should read --0.5 mM DTT--

Signed and Sealed this
Fourth Day of November, 2014

Michelle K. Lee
*Deputy Director of the United States Patent and Trademark Office*

Line 34, "y-[$^{32}$P]ATP" should read --γ-[$^{32}$P]ATP--

Column 18,
Line 65, "cucurbitacin 1" should read --cucurbitacin I--

Column 19,
Line 1, "Biochem. 1997" should read --Biochem. J. 1997--
Line 21, "Pane-1" should read --Panc-1--
Line 33, "NTII 3T3" should read --NIH 3T3--

Column 20,
Line 13, "BI-124" should read --JSI-124--

Column 21,
Lines 29-30, "Erk1 /Erk2,,TNK1, and Akt" should read --Erk1/Erk2, JNK1, and Akt--
Line 47, "(STAT3-13)" should read --(STAT3-β)--

Column 22,
Line 28, "v-Src/NIH 313" should read --v-Src/NIH 3T3--

Column 23,
Line 56, "cucurbitacin ID" should read --cucurbitacin D--